US006610494B2

(12) United States Patent
Marquardt et al.

(10) Patent No.: US 6,610,494 B2
(45) Date of Patent: Aug. 26, 2003

(54) SOLID-PHASE ACTIVITY ASSAY FOR BIOLOGICALLY ACTIVE SUBSTANCE

(76) Inventors: Ronald R. Marquardt, University of Manitoba, Dept. of Animal Science, Winnipeg, Manitoba R3T 2W2 (CA); Xiao Hao, Kinetek Biotechnology Corporation, 500-524, Vancouver, British Columbia (CA), V5Z 1A1; Guojie Wang, Nanjing Agricultural University, Laboratory Animal Physiology and Biochemistry, Nanjing (CN), 210095; Zhiqun Zhang, Nanjing Agricultural University, Laboratory Animal Physiology and Biochemistry, Nanjing (CN), 210095; Zhibo Gan, 99 Dalhousie Drive, Apt. 212, Winnipeg, Manitoba R3& 3M2 (CA)

( * ) Notice: Subject to any disclaimer, the term of this patent is extended or adjusted under 35 U.S.C. 154(b) by 18 days.

(21) Appl. No.: 09/180,819

(22) PCT Filed: May 13, 1997

(86) PCT No.: PCT/US97/07983
§ 371 (c)(1),
(2), (4) Date: May 20, 1999

(87) PCT Pub. No.: WO97/43438
PCT Pub. Date: Nov. 20, 1997

(65) Prior Publication Data
US 2002/0164638 A1 Nov. 7, 2002

Related U.S. Application Data
(60) Provisional application No. 60/017,659, filed on May 14, 1996.

(51) Int. Cl.⁷ .......................................... G01N 33/533
(52) U.S. Cl. ........................... 435/7.1; 435/5; 435/7.9; 435/6; 435/28; 436/172; 436/518; 514/12
(58) Field of Search ......................... 435/7.1, 5, 6, 28, 435/7.9; 436/172, 518; 514/12

(56) References Cited

U.S. PATENT DOCUMENTS

| | | | | |
|---|---|---|---|---|
| 4,016,043 A | | 4/1977 | Schuurs et al. | |
| 4,328,313 A | * | 5/1982 | Simonson et al. | 435/200 |
| 4,444,879 A | * | 4/1984 | Foster et al. | 435/7 |
| 4,822,516 A | * | 4/1989 | Suzuki et al. | 252/174.12 |
| 4,859,581 A | * | 8/1989 | Nicolson et al. | 435/4 |
| 5,087,561 A | * | 2/1992 | Rosenblatt et al. | 435/7.21 |
| 5,183,826 A | * | 2/1993 | Bills et al. | 514/411 |
| 5,416,003 A | * | 5/1995 | Lawrence et al. | 435/18 |
| 5,561,051 A | * | 10/1996 | Silverman | 435/18 |
| 5,571,684 A | * | 11/1996 | Lawrence et al. | 435/18 |
| 5,585,273 A | * | 12/1996 | Lawrence et al. | 435/288.7 |
| 5,710,174 A | * | 1/1998 | West et al. | 514/450 |
| 5,747,276 A | * | 5/1998 | Hoch et al. | 435/32 |
| 5,747,296 A | * | 5/1998 | Moyle et al. | 435/72 |
| 5,792,499 A | * | 8/1998 | Atwell | 426/549 |
| 5,804,380 A | * | 9/1998 | Harley et al. | 435/6 |
| 5,814,460 A | * | 9/1998 | Venton et al. | 435/7.1 |
| 5,821,331 A | * | 10/1998 | Hammand et al. | 530/331 |
| 5,830,888 A | * | 11/1998 | Getman et al. | 514/183 |
| 5,840,509 A | * | 11/1998 | Ni et al. | 435/23 |
| 5,856,083 A | * | 1/1999 | Chelsky et al. | 435/4 |
| 5,856,300 A | * | 1/1999 | Rittershaus et al. | 514/21 |
| 5,872,210 A | * | 2/1999 | Medabalimi | 530/327 |
| 5,876,945 A | * | 3/1999 | Chisholm et al. | 435/7.1 |
| 5,876,946 A | * | 3/1999 | Burbaum et al. | 514/7.1 |
| 5,919,900 A | * | 7/1999 | Moyle et al. | 530/350 |
| 5,972,625 A | * | 10/1999 | Rosen et al. | 435/7.2 |
| 5,981,167 A | * | 11/1999 | Taremi et al. | 435/4 |
| 6,013,466 A | * | 1/2000 | Black et al. | 435/23 |
| 6,043,045 A | * | 3/2000 | Hoch et al. | 435/17 |
| 6,110,696 A | * | 8/2000 | Brown et al. | 435/7.6 |
| 6,121,027 A | * | 9/2000 | Clapper et al. | 435/180 |
| 6,121,296 A | * | 9/2000 | Schramm et al. | 514/343 |
| 6,127,139 A | * | 10/2000 | Te Koppele et al. | 435/24 |
| 6,159,746 A | * | 12/2000 | Islam et al. | 436/518 |
| 6,243,980 B1 | * | 6/2001 | Bronstein et al. | 435/7.72 |
| 6,337,386 B1 | * | 1/2002 | Shone et al. | 530/329 |

FOREIGN PATENT DOCUMENTS

WO        95/26505    * 10/1995       G01N/33/573

OTHER PUBLICATIONS

US 6,057,286, 5/2000, Harrison et al. (withdrawn)*
Wang, Gary T et al, Tetrahedron Letters, vol. 31(45), pp. 6493–6496, 1990.*
White, B.A et al, Applied and Environmental Microbiology, vol. 54(6), pp. 1634–1636, Jun. 1988.*
Miyoshi, L et al, Analytical biochemistry, Ma 1, 1996, vol. 236(2), pp. 360–363.*
Wondrak, EM et al, Analytical Biochemistry, vol. 188, pp. 82–85, pp. 1990.*
Fournout et al, Analytical Chemistry, vol. 69, pp. 1746–1752, 1997.*

* cited by examiner

Primary Examiner—Lynette R. F. Smith
Assistant Examiner—Ginny Allen Portner
(74) Attorney, Agent, or Firm—Kohn & Associates, PLLC

(57) ABSTRACT

A method of detecting via a solid-phase assay the amount of biological activity, identity and/or the quantity of a biologically active substance is disclosed. The method utilizes the biological activity of the substance itself to provide the method of detection. The method provides competitive and noncompetitive assays.

6 Claims, 9 Drawing Sheets

SOLID-PHASE ACTIVITY ASSAY FOR BIOLOGICALLY ACTIVE SUBSTANCE

CROSS-REFERENCE TO RELATED APPLICATION

This application claims the benefit of priority of PCT Application No. PCT/US97/07983, filed May 13, 1997, which claims benefit of priority under 119(e) U.S. Provisional Patent Application No. 60/017,659, filed May 14, 1996, both of which are incorporated herein in their entirety.

BACKGROUND OF THE INVENTION

1. Technical Field

This present invention relates generally to methods of detecting and determining the identity, amount and activity of molecules with biological activity. More specifically, the present invention is concerned with a method of measuring the amount and activity of enzymes, enzyme inhibitors, lectins, receptors and other biologically active molecules via solid-phase assay techniques.

2. Background Art

Binder-ligand assays, such as immunoassays, are well known in the art and are used to quantitate the presence of a substance utilizing antibody based identification. (see Stites et al, Basic and Clinical Immunology, 8th edition, Appleton & Lange, pgs 170–176 for a review). However, immunoassays have two disadvantages. The first disadvantage is that they require an antibody raised against the substance of interest. In the second, if the substance being identified has biologically activity, for example an enzyme, the immunoassay cannot determine the level of activity of the substance, only its presence.

There are assays for enzyme activity, receptor function and the like, but it would be useful to have such assays utilizing solid-phase technology and accuracy with minimal preparation of components, i.e. no physical separation step, and that can be readily adapted to a routine assay of large number of samples.

As an example, enzymes play a key role in biochemical reactions. The determination of their activity is important in all fields related to biology such as medicine, food and pharmacy. The methods currently used for enzyme assays are mainly based on the formation of product from substrate following enzyme catalysis (Loround, 1981; Rossomando, 1990). Although these methods are the mainstream of much biological research there is also a need to not only determine the activity of an enzyme but also the quantity of enzyme present as well as its identity. This is particularly important for an enzyme for which its activity does not follow normal Michaeleus-Menton kinetics such as the allosteric enzymes or those that are activated by covalent modification.

In addition there is a need for the quantitative determination of the amount of enzyme inhibitor that may be present in a biological system. This is particularly important in the medical field where much attention has been directed towards the discovery of inhibitors of certain enzymes in AIDS research (Miller et al, 1989) or the development of inhibitors for the control of blood pressure (Ondetti et al., 1982) or the hydrolysis of antibiotics including penicillin (Cullman, 1990).

There is also a urgent demand for enzyme assays that can be automatized especially in the pharmaceutical industry as enzyme are usually used as a target for drug discovery. Thousands of chemical compounds must be screened for the search for new drugs. The development of a new method for the assay of enzymes that is amenable to high throughput screening and automation would not only greatly facilitate such screening but would also have many other applications and would result in markedly reduced costs. In addition to enzymes, highly automated, screening assays for measurements of receptors and lectins are also needed.

For example, there has been a continuing interest in the development of simple and reliable assay procedures for β-glucanase, as this enzyme plays an important role in the depolymerization of barley β-glucan in both the brewing and the poultry production industries. Several methods have been reported for this assay including viscometry (Bourne and Pierce, 1970), reducing sugar production (Denalt et al., 1978), radial gels diffusion (Edney et al., 1986; Martin and Bamforth, 1983) and the use of azo-barley glucan (McCleary and Shameer, 1987). The detection and the quantitation of enzyme activity in finished feeds by any method developed to date is technically challenging due to the requirement for high sensitivity and the complex nature of feed itself. The development of a highly sensitive photometric method will be welcomed particularly if this could lead to a high degree of assay automation. Microtitration using micro-titre plates and a microtitre plate reader would greatly facilitate such an assay.

There have been two approaches in this direction, one was the studies of Wirth and Wolf (1992) using a micro-plate calorimetric assay. The principle of this assay is the same as the azo-barley glucan method except the absorbency is read in microtitre plate wells. This procedure, as well as the original azo-barley glucan procedure, has the disadvantage of requiring a precipitant and a centrifuging step. It also does not have a high degree of sensitivity. Another approach has been to quantitate the amount of enzyme using the immunological properties of enzymes (Bühler, 1991; Rafael et al., 1995). The main drawback of this technique is its inability to assess the biological activity of a particular enzyme, as the immunoassay will estimate the amount of enzyme protein but not its biological activity. Also this assay would only be useful for enzyme from closely related species as antibodies tend to have high specificity. In a recent review Headon (1993) concluded that no suitable method has been reported that facilitates detection and quantitation of enzymes added to feed. This may in part be attributed to the lack of an assay that is able to detect the very low levels of enzymes that are usually added to feed.

Additionally, the availability of a simple, sensitive and efficient method for the assay of protease activity would be very useful for the recombinant protein industry to test intrinsic proteolytic activity, drug discovery to screen for protease inhibitors, diagnostics and routine research. However, the current commonly used methods cannot fulfill these requirements because of insufficient sensitivity (e.g. casein gel), complicated manipulations (e.g. trichloroacetic acid precipitation, centrifugation and heating), radioactive hazard (e.g. radio labelled substrates) and expensive equipment required (e.g. fluorescence polarization analyzer), etc. These procedures are usually time-consuming and often do not lend themselves to automation.

SUMMARY OF THE INVENTION

According to the present invention, a method of detecting via a solid-phase assay the amount of biological activity and/or the quantity of a biologically active substance is disclosed. The method utilizes the biological activity itself of the substance to provide the method of detection.

In an embodiment of the present invention a method of detecting via a solid-phase assay the amount of biological activity of a biologically active substance utilizing the biological activity is disclosed. A first component is bound to a surface wherein the first component is conjugated to a first indicator. A sample is contacted to the first component. The sample contains a second component having unknown biological activity which is to be measured. The components are in a reaction mixture under conditions such that the biological activity between the first and second component will unbind the first component. After the reaction is complete, the sample is removed. The amount of bound first component remaining is measured. There is a reciprocal relationship between the amount of biological activity and the remaining bound first component.

In a further embodiment of the present invention a method for detecting via a solid-phase assay the amount of an inhibitor of biological activity of a biologically active substance utilizing the inhibition of biological activity is disclosed. A first component is bound to a surface wherein the first component is conjugated to a first indicator. A sample is contacted to the first component. The sample contains a second component having a known amount of a second component having known biological activity and an unknown amount of a third component which is an inhibitor of the second component. The components are allowed to react for a predetermined time under conditions such that the biological activity between the first and second component will unbind the first component and the third component will interfere with the reaction between the first and second component. After the reaction is complete, the sample is removed. The amount of bound first component remaining is determined wherein there is a direct relationship between the remaining bound conjugated first component and amount of the third component in the sample.

The present invention also provides a method of detecting via a solid-phase assay the identity of a biologically active substance utilizing inhibition of the biological activity. A first component conjugated to a first indicator is bound to a surface. A sample is contacted to the first component. The sample contains a second component having a generally known biological activity but is unknown as to its specific activity. The sample also contains a known amount of a third component which is one of a potential inhibitor of the second component. The assay includes a panel of such potential inhibitors. The reaction is allowed to occur under conditions such that the biological activity between the first and second component will unbind the first component and the third component can interfere with the reaction between the first and second component if it is specific for the second component.

After a predetermined time, the sample is removed, generally by washing as is known in the art. The amount of bound first component remaining is determined. If there is a reduction of the amount of the bound first component than the third component did interfere with the reaction between the first and second component thereby identifying the second component. If there is no significant reduction of bound first component than the selected specific inhibitor did not interfere and the second component is not identified. Appropriate standard curves are performed as is known in the art.

The present invention also provides for competitive assays between a first and second component based on the biological activity of the second component.

In a first pair of solid-phase competitive assays the method determines the quantity of a biologically active substance utilizing the biological activity of the substance. A known quantity of a first component which binds to a biologically active second component is bound to the surface of a reaction vessel. A sample or extract containing an unknown quantity of the second component having biological activity is added. The sample also contains a known quantity of the second component coupled to a first indicator. The reaction is run under conditions such that the first and second component will bind due to the biologic activity. After a predetermined time the sample is removed as is known in the art. The amount of second component coupled to a first indicator bound to the first component is then determined. There is a reciprocal relationship between the quantity of the second component coupled to a first indicator bound to the first component and the unknown quantity of the second component having biological activity in the sample. Appropriate standard curves as is known in the art allows quantitation.

In the alternative assay the sample contains an unknown quantity of the first component and a known quantity of the second component coupled to a first indicator. There is a reciprocal relationship between the quantity of the second component coupled to a first indicator bound to the bound first component and the unknown quantity of the first component in the sample.

A second pair of competitive solid-phase assays also provides a method of detecting the quantity of a biologically active substance utilizing the biological activity of the substance. In these assays a known quantity of a second component having biological activity is bound to the surface of a reaction vessel. A sample containing an unknown quantity of the second component and a known quantity of a first component coupled to a first indicator is added. The reaction is run under conditions such that the first and second components will bind due to biologic activity. The sample is removed the sample after the reaction is complete. The amount of first component coupled to a first indicator bound to the bound second component is determined. There is a reciprocal relationship between the quantity of the bound first component coupled to an indicator and the unknown quantity of the second component in the sample.

In the alternative assay of this pair, the sample contains a known quantity of the first component coupled to a first indicator and an unknown quantity of the first component. After the reaction is complete, the amount of first component coupled to a first indicator bound to the bound second component is determined. There is a reciprocal relationship between the quantity of the bound first component coupled to an indicator and the unknown quantity of the first component in the sample.

In these competitive assays the second component can be an enzyme and the first component an inhibitor of the enzyme. Alternatively, the second component is a lectin and the first component is a lectin-binding substance. Further, the assays can use a receptor as the second component and the first component a receptor-binding substance.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
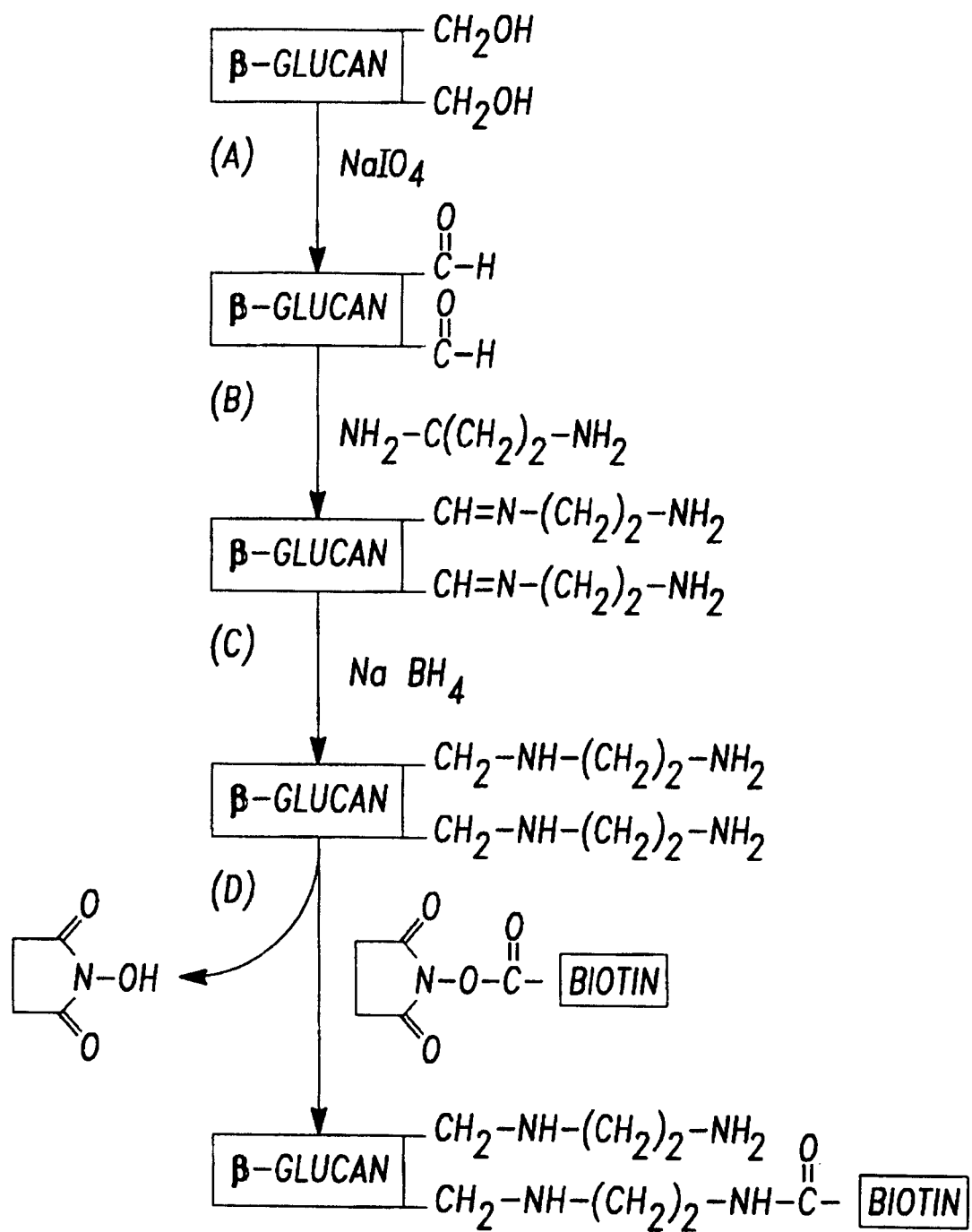
FIG. 1 is a schematic of the synthesis of biotinylated β-glucan. The hydroxyl groups of β-glucan are partially oxidized to an aldehyde with $NaIO_4$ (A) followed by reaction with ethylenediamine $[NH_2(CH_2)_2NH_2]$ (B). The Schiff bases that are formed are reduced with NaBH$_4$ (C) followed by reaction of the free amide groups of the β-glucan-ethylenediamine complex with N-hydroxysuccinimide ester of biotin (BNHS) to form biotinylated β-glucan (D).

According to the present invention, a method of detecting via a solid-phase assay, the amount (rate, degree) of biological activity and/or quantity and identity of a biologically active substance is disclosed. The assay utilizes the biological activity of the substance itself to measure the activity, quantity or identity of the substance itself. The assay does not utilize antibodies.

In general as is known for solid-phase assays, a first component is bound to the surface of a reaction vessel. A sample is then contacted (applied) to the first component in a reaction mixture containing an indicator molecule. The sample contains a second component which has a biologic activity. A reciprocal protocol can used, that is the second component bound and the sample containing the first component. There is an interaction between the first and second components caused by the biologic activity, the interaction causes changes in an indicator molecule.

By biological activity and/or biologically active substance is meant any biological molecule which acts upon a second molecule such to change or bind the second molecule (a ligand) and which can be active in, part of, or derived from a living system/organism. Examples of such molecules are enzymes, lectins, receptors and cell adhesion molecules.

The solid-phase assay can be competitive or non-competitive and generally involves two components. One of the components has biological activity (generally referred to herein as the second component) and the other component (generally referred to as the first component) is acted on, bound to or interferes with (inhibitor) the second component due to the biological activity of the second component. For example the two components can be an enzyme and its substrate, an enzyme and an inhibitor of the enzyme, lectins and lectin binding substances, receptors and receptor binding substances and adhesion molecules and cell surface molecules.

The assay requires the binding of one of the components of the assay to the surface of a reaction vessel. In general the assay binds the first component but the reciprocal, i.e. binding of the second component, is also provided in the present invention. Known methods for binding (or coating) the surface of the reaction vessel with one of the assay components can be utilized in the invention embodiments described herein. In general the binding methods utilize charge differences to bind the component to the surface. Methods involving "sandwich" techniques can be used as are known in the art for enzyme immunoassays (EIA). For example, antibodies to the component can be bound to the surface and in turn bind the component. The selected method will be display the component in the assay such that stearic hinderance is minimized and component amount optimized for the assay embodiment. In a preferred embodiment the reaction vessel is a microtiter plate.

Further the method requires the conjugation (labeling) of one of the components of the assay to an indicator molecule which is used for quantitation. The component can be randomly labelled throughout or can be labeled at only one position as is appropriate for the cleavage site(s), binding site(s) or activity assay.

The measurement can be indirect or direct. For indirect, the indicator molecule can involve an coupling system such as biotin-avidin (or streptavidin). One component of the system is labeled with biotin. The avidin is conjugated to a label such as alkaline phosphatase, horseradish peroxidase, colored dye, fluorescent molecule, luminescent molecule, β-galactosidase, urease, tritium, $^{14}C$ and iodination. Although indicator labeled avidin or streptavidin can be used to detect the biotinylated substrate other binding couples could also be used. Requirements of such couples are that they have a low binding constant, are stable under the condition of the assay, are specific, do not increase background values, and do not interfere with the assay. Other coupling pairs are the reaction between an inhibitor and its biologically active target substance or between a carbohydrate and a lectin. For example, to use mannose or glucose instead of biotin and use a corresponding labeled lectin in place of avidin, i.e. as the coupling pair. Methods for measuring these labels are known to those skilled in the art and Examples are presented herein.

Alternatively, a direct measurement of the labeled component can be utilized. Indicators (label) such as alkaline phosphatase, horseradish peroxidase, colored dye, fluorescent molecule, luminescent molecule, β-galactosidase, urease, tritium, $^{14}C$ and iodination can be used.

As described herein, the reaction mixture of the components is established under conditions such that the biologically activity between the components is maintained. In general, the biologically active component when reacting with the other component will change the amount of label available for measurement. For example, when the biologically active second component is an enzyme, it will unbind, i.e. cleave, its substrate (first component) from the surface to which it is bound. These conditions are established as described herein for each set of biologically active components.

Receptors in general will bind to their ligand as will cell adhesion molecules and lectins and competitive assays are necessary for their measurement. Lectins have been defined as being protein (glycoprotein) of a non-immunoglobulin nature capable of specific recognition and reversible binding to carbohydrate moieties of complex carbohydrates without altering covalent structure of any of the recognized glycosyl ligands. A second definition is that lectins are protein (or glycoprotein) of nonimmune origin which agglutinate cells and/or precipitate glycoconjugates. Lectins usually react with the non-reducing end of oligo or polysaccharide and tolerate little variation at C-3 or C-4 but C-2 appears to be critical (For a detailed review, see Lectins, by Pusztai, 1989). Assays therefore are available that can detect lectins (hemagglutinin) or the compounds that they bind.

The sample may be an extract from a product which may contain the biologically active component to be identified or to quantify the amount of activity or quantity of the component. As the present invention utilizes a solid-phase assay, the sample/extract does not need to be purified and can be applied directly. Non interacting (binding) elements of the extract are remove, i.e. washed away. Therefore the present method does not require physical extraction of the substance to be measured from the extract.

As described, after reacting the sample is removed, generally by washing as is known in the EIA art, from the reaction vessel (microtiter well). The amount of bound indicator remaining is then determined. In a preferred embodiment a calorimetric assay is utilized which enables the use of enzyme linked immunosorbent assay (ELISA) plate readers and related technologies.

The method of the present invention provides for detecting via a solid-phase assay the amount of biological activity of a biologically active substance utilizing the biological activity. In this assay a first component which is conjugated to a first indicator is bound to the surface of the reaction vessel. A sample is then contacted (applied) to the reaction vessel containing the bound first component. The sample contains a second component. The second component has biological activity but the amount (rate) is unknown and is to be determined by the assay. The components are in a reaction mixture under conditions that maintains the biological activity between the first and second components. In this assay the activity results in the unbinding of the first component from the surface or a portion of the molecule thereof. That is the second component will hydrolyze or otherwise remove the labeled first component from the surface. The sample is then removed after allowing the reaction to proceed for a defined time.

The amount of bound first component remaining after the reaction is then measured as described herein above. There is a reciprocal relationship between the amount of biological activity and the remaining bound first component. That is, the more active the second component the less bound first component.

The method can be used where the second component is an enzyme and the first component is a substrate for the enzyme. The enzyme can be capable of degrading a substrate selected from the group consisting of polymeric and non-polymeric substrates. Polymeric substrates are substrates which can be cleaved in at least two positions and can be proteins, polypepetides, carbohydrates, DNA and RNA. Nonpolymeric substrates can also be selected peptide, carbohydrate molecules and nucleic acid sequences which can only be cleaved by the enzyme at one position (site).

For example, protein substrates which can be used for a selected protease are casein, albumin, collagen and gelatin. In an alternative example, the enzyme is β-glucanase and the substrate is glucan, or the enzyme is xylanase and the substrate arbinoxylan or the enzyme is cellulase and the substrate cellulose.

As discussed herein above, determining the amount of remaining bound first component conjugated (coupled) to an indicator can be using an indirect label such as biotin-avidin (avidin coupled to alkaline phosphatase) or a direct label such as alkaline phosphatase. A preferred calorimetric assay can then be used. As appropriate for the assays, calibration or standard curves will be made so that quantitation can be determined as is known in the art.

For labeling of the polymeric substrate (first component), the biotin or other label is coupled throughout the molecule. As the enzyme cleaves the molecule at the multiple cleavage sites, more label is removed thereby indicating activity of the enzyme.

For nonpolymeric substrates, i.e. having one cleavage site, the first component is directly or indirectly bound to a surface while the another portion of the molecule is labeled directly or indirectly to an appropriate indicator molecule. Cleavage of the substrate by second component, in this example an enzyme, will release the indicator molecule into the media which is removed, generally by washing. The residual labeled molecule can be quantitated and related to activity of the biologically active substance. For example, a peptide substrate for an enzyme is bound through terminal carboxyl of the peptide to a surface. The terminal amino group is coupled to a first indicator molecule either for direct measurement or in an indirect assay. After reaction, the amount of unhydrolyzed substrate which contains the label can be quantitated and this is reciprocally related to protease activity.

The present invention also provides a method for detecting via a solid-phase assay the amount of an inhibitor of biological activity of a biologically active substance utilizing the inhibition of biological activity. In this assay the first component is bound to a surface of a reaction vessel. The first component is conjugated to a first indicator. A sample containing a known amount of a second component is added to the first component in the reaction vessel. The second component has a known biological activity. The sample also contains an unknown amount of a third component which is an inhibitor of the second component. The components are allowed to react for a predetermined time under conditions such that the biological activity between the first and second component will unbind the first component and the third component will interfere with the reaction between the first and second component. After the reaction is complete, the sample is removed.

The amount of bound first component remaining after the reaction is determined as described herein above. There is a direct relationship between the remaining bound conjugated first component and amount of the third component in the sample. That is the less inhibitor in the reaction the less label since the reaction between the first and second component will not be inhibited. The more inhibitor in the sample the more label will be measured.

As described herein above, polymeric and nonpolymeric first components (substrates) can be used in the assay and labeled as described.

In a third embodiment, a method of detecting via a solid-phase assay the identity of a biologically active substance utilizing inhibition of the biological activity is disclosed. As in the previous two assays described herein above, a first component conjugated to a first indicator is bound to a surface. A sample is contacted to the first component. The sample contains a second component having a generally known biological activity but is unknown as to its specific activity. For example, the second component is a protease but it is not known which specific protease it is. The sample also contains a known amount of a third component which is one of a potential inhibitor of the second component. The assay includes a panel of such potential inhibitors. The reaction is allowed to occur under conditions such that the biological activity between the first and second component will unbind the first component and the third component can interfere with the reaction between the first and second component if it is specific for the second component.

After a predetermined time, the sample is removed, generally by washing as is known in the art. The amount of bound first component remaining is determined. If there is a reduction of the amount of the bound first component than the third component did interfere with the reaction between the first and second component thereby identifying the second component. If there is no significant reduction of bound first component than the selected specific inhibitor did not interfere and the second component is not identified. Appropriate standard curves are performed as is known in the art.

The present invention also provides for competitive assays between a first and second component based on the biological activity of the second component.

In a first pair of solid-phase competitive assays the method determines the quantity of a biologically active substance utilizing the biological activity of the substance. A known quantity of a first component which binds to a biologically active second component is bound to the surface of a reaction vessel. A sample or extract containing an unknown quantity of the second component having biological activity is added. The sample also contains a known quantity of the second component coupled to a first indicator. The reaction is run under conditions such that the first and second component will bind due to the biologic activity. After a predetermined time the sample is removed as is known in the art. The amount of second component coupled to a first indicator bound to the first component can then be determined as described herein above. There is a reciprocal relationship between the quantity of the second component coupled to a first indicator bound to the first component and the unknown quantity of the second component having biological activity in the sample. That is the more label the less of the unknown amount of the second component. Appropriate standard curves as is known in the art allows quantitation.

In the alternative assay of the pair, the sample contains an unknown quantity of the first component and a known quantity of the second component coupled to a first indicator. There is a reciprocal relationship between the quantity of the second component coupled to a first indicator bound to the bound first component and the unknown quantity of the first component in the sample.

In these assays the second component can be an enzyme and the first component an inhibitor of the enzyme. In one example, trypsin is the enzyme and the inhibitor is ovomucoid or leupeptin. Alternatively, the second component is a lectin and the first component is a lectin-binding substance. Further, the assays can use a receptor as the second component and the first component a receptor-binding substance. Still further, a cell adhesion molecule and its cell surface binding molecule can be used such as CD2 and the cell surface molecule, LFA-3.

The interaction of receptor with its particular binding agent (ligand) has the same principal as that for the enzyme—enzyme inhibitor assay or the lectin—lectin binding agent. As such either ligand or receptor is coated onto the plate and the amount of receptor or ligand quantitated using a competitive type assay. Under such condition either the ligand or the receptor would be tagged with an appropriate indicator molecule depending on whether receptor or ligand is being quantitated.

A second pair of competitive solid-phase assays also provides a method of detecting the quantity of a biologically active substance utilizing the biological activity of the substance. In these assays a known quantity of a second component having biological activity is bound to the surface of a reaction vessel. A sample containing an unknown quantity of the second component and a known quantity of a first component coupled to a first indicator is added. The reaction is run under conditions such that the first and second components will bind due to biologic activity. The sample is removed the sample after the reaction is complete. The amount of first component coupled to a first indicator bound to the bound second component is determined. There is a reciprocal relationship between the quantity of the bound first component coupled to an indicator and the unknown quantity of the second component in the sample.

In the alternative assay of this pair, the sample contains a known quantity of the first component coupled to a first indicator and an unknown quantity of the first component. After the reaction is complete, the amount of first component coupled to a first indicator bound to the bound second component is determined. There is a reciprocal relationship between the quantity of the bound first component coupled to an indicator and the unknown quantity of the first component in the sample.

In these assays also the second component can be an enzyme and the first component an inhibitor of the enzyme. In one example, trypsin is the enzyme and the inhibitor is ovomucoid or leupeptin. Alternatively, the second component is a lectin and the first component is a lectin-binding substance. Further, the assays can use a receptor as the second component and the first component a receptor-binding substance. Still further, a cell adhesion molecule and its cell surface binding molecule can be used.

The present invention also provides kits for the above assays. The kits in addition to the appropriate buffers for each component including enzymes, substrates and/or inhibitor, lectins and lectin-binding substance (ligands), purified receptors and receptor-binding substance (ligand), cell adhesion molecules and cell surface binding molecules and also provides standards and reaction vessels. The reaction vessels can be precoated with the first or second component as appropriate for the assay including but not limited to enzymes, receptors, lectins, lectin-binding and receptor binding substances as appropriate. Further the kit includes appropriately labeled components and inhibitor, including but not limited to enzymes, receptors, lectins, lectin-binding and receptor binding substances. The kit can also include the materials necessary for the colorimetric or other assays employed in determining the amount of label (indicator) for the assay remaining in the reaction vessel.

Figure 2:
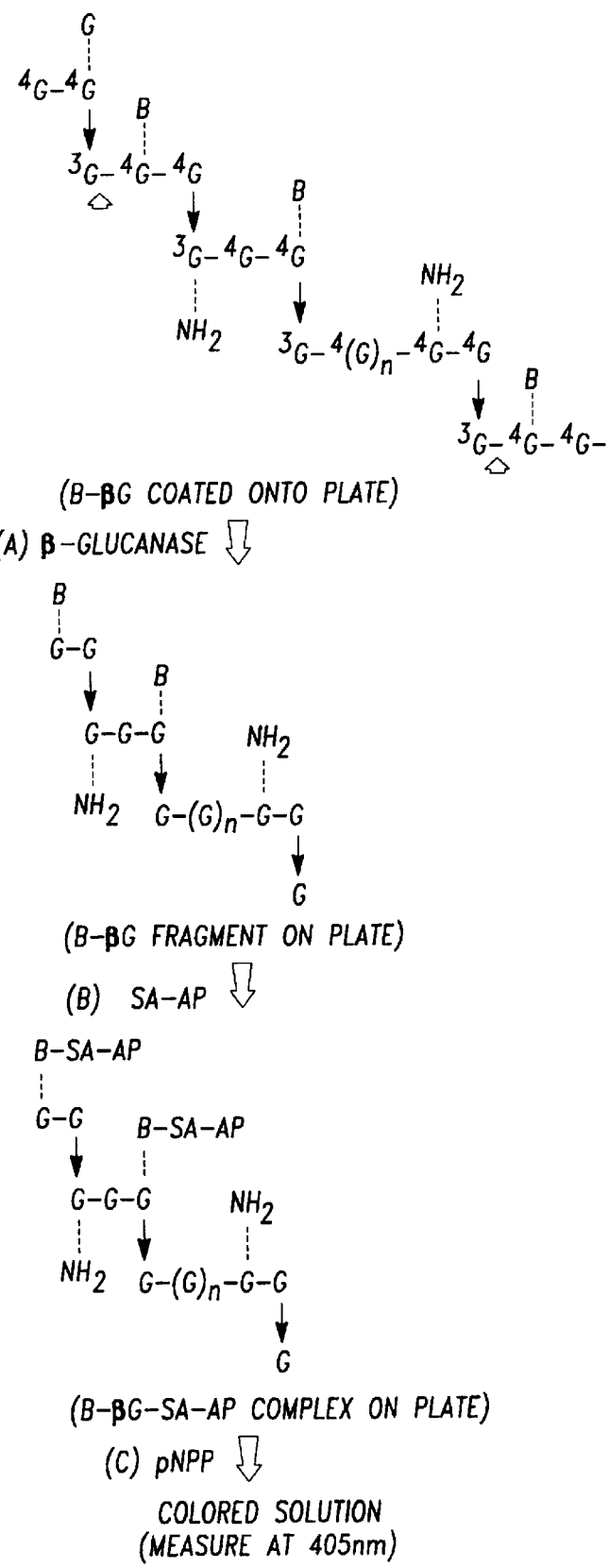
FIG. 2 is a schematic of the steps in the ELSA for β-glucanase. The substrate, biotinylated-β-glucan (B-βG), is incubated with β-glucanase (lichenase) and the hydrolysed substrate is removed by washing (A). Excess alkaline phosphatase-streptavidin complex (SA-AP) is then incubated with hydrolyzed B-βG followed by washing to remove unreacted SA-AP (B). The amount of SA-AP bound to the unhydrolyzed substrate (B-βG) is quantitated by incubating with pNPP (C). Arrows indicates bonds hydrolyzed by the β-glucanase.

In Example 1 a simple, sensitive avidin-biotin enzyme-linked sorbent assay (ELSA) for β-glucanase using aminated and biotinylated glucan as substrate (FIG. 1) was developed utilizing the method of the present invention. In this assay the substrate is incubated with β-glucanase and the amount of β-glucan-biotin remaining on the titre plate is quantitate enzymatically following the binding of an alkaline phosphatase-streptavidin complex to the unreacted substrate complex (FIG. 2). The color produced by the activity of the bound alkaline phosphatase in turn can be indirectly related to the activity of the enzyme in the well. The use of second enzyme not only greatly amplifies the signal but provides the basis for the development of a simple method for monitoring β-glucanase activity.

Partial hydrolysis of this substrate with β-glucanase was shown, the reaction of the biotin from the unhydrolysed substrate with an alkaline phosphatase-streptavidin complex and finally the quantitation of the amount of beta-glucan remaining on the plate using alkaline phosphatase is demonstrated. The activity of the bound indicator enzyme, alkaline phosphatase, in the optimized assay is proportionally related to the β-glucanase activity in the sample. The ELSA is simple, as the hydrolysed β-glucan fragments can be readily separated from the unhydrolyzed substrate by a washing step, and is adapted to the routine assay of a large number of samples (as many as 200 per person/day), has good precision (CV=4.0 to 6.4%) and high sensitivity (detects as low as 0.001 mU of β-glucanase/assay). A similar type assay was also developed for xylanase using biotinylated arabinoxylan. The ELSA developed in Example 1 provides a simple and highly sensitive procedure using the present invention for the assay of β-glucanase and xylanase.

In Example 2 a specific method for not only quantitating the amount of enzyme in a sample but also for quantitating the concentration of its inhibitor is presented using the method of the present invention. The assay, which is referred to as a biotinylated enzyme inhibitorsorbent assay (BEISA), is based on the specific binding of a biotin-labelled enzyme with its corresponding inhibitor. In this assay, the inhibitor is coated onto the surface of a plastic as is present in a titre plate well. A known amount of biotin-labelled enzyme and an unknown amount of the enzyme to be quantitated are mixed and allowed to compete for the immobilized inhibitor. The enzyme-biotin complex that is bound by the inhibitor is then allowed to bind quantitatively with an indicator enzyme such as a streptavidin-alkaline phosphatase conjugate. The avidin-phosphatase complex that has been immobilized is then allowed to react with one of the substrates for phosphatase to produce a colored solution. The intensity of color produced by this reaction is reciprocally related to the unknown amount of enzyme in the sample. The actual amount of enzyme in solution can be estimated from a standard curve prepared from known concentrations of the enzyme.

The amount of inhibitor in a sample can also be quantitated using the same assay. In this procedure, the inhibitor to be quantitated and the inhibitor immobilized on the surface of a plastic compete with each other for the biotinylated enzyme that is present in solution. The avidin-phosphatase conjugate is then allowed to react, quantitatively with the enzyme-biotin complex that is coupled to the immobilized inhibitor followed by color development. The unknown concentration of the inhibitor can be determined from a standard curve prepared from known concentrations of the inhibitor and is reciprocally related to the intensity of color that is produced by the bound avidin-phosphatase conjugate.

In Example 3 a solid phase biotinylated casein assay demonstrates the method of the present invention for proteases and protease inhibitors. The binding of the substrate to a solid phase greatly facilitate the subsequent steps in the assay such as washing to remove hydrolysed products or unreacted reagents while the use of a labelled substrate allows for the ready analysis of the amount of substrate that remains. The binding of biotin, a relatively small molecule, to the substrate avoids stearic interfere that may occur with larger indicator molecules and also provides considerable flexibility in the type of indicator that can be used as the biotin will react with any indicator provided it is conjugated to avidin, a protein that has a high affinity for biotin (Green, N. M., 1963). Also, the use of an enzyme such as alkaline phosphatase as the indicator molecule, rather than a colored molecule, allows for a markedly amplified signal since each phosphatase can generate many colored molecules. The adaptation of the entire process to a titre plate formate and the use of an ELISA reader that is coupled to a computer to measure absorbency and calculate results greatly facilitated the analysis of many samples in a relatively short period of time. In addition, the assay requires only small amounts of reagents, and has good sensitivity and accuracy and can be completed in a relatively short period of time. The assay, as a result, can be automated and is suitable for the analysis of a large number of samples.

The sensitivity of the biotinylated casein method, under the experimental conditions as given in Example 3, is less than the radioactive assay (Sevier, E. D., 1976), FTC-casein method (Twining, S. S., 1984), $FITC_{25}BSA$ method (Voss, et al, 1996) and FP method (Bolger et al, 1994). It, nevertheless, fulfills the essential requirements of most protease assays and has the capability of testing the activity (i.e., $10-10^6$ ng trypsin/100 ul/sample) of protease over a wide range of activities. Also the nature of the assay, as indicated in results, allows considerable flexibility in its design and therefore in its corresponding sensitivity. Applicants have demonstrated that the sensitivity of the assay can be increased by increasing the degree that the substrate is biotinylated, by decreasing the amount of substrate that is coated onto the wells of the titre plate, and by increasing the duration of the hydrolysis time. These changes can produce dramatic improvements in sensitivity but in some cases corresponding increases in the time required to produce the desired absorbency changes is required. This later problem, however, can be solved by the use of different indicator enzymes such as horseradish peroxidase which have a higher turnover or by the use of an avidin complex that has multiple units of the indicator bound to it. Under such conditions it will be possible to not only develop more sensitive protease assays but also to have an assay that can be completed in a relatively short period of time.

Although α-casein was selected as the substrate for this assay, other proteins can also be used if they prove to be more suitable for a particular assay or group of assays. Also, as indicated in the results, the class of protease in the sample can be readily identified if the assay is coupled with the use of a battery of different inhibitors, each of which can inhibit the different classes of protease. In addition, the assay can also be modified for the determination of the concentration of specific protease inhibitors.

Overall, this paper reports on the development of a new type of assay for proteases and protease inhibitors that is sensitive, accurate, simple, rapid, and readily adapted to the specificities of the sample to be assay. The assay is also inexpensive to carry out, can utilize equipment that is present in most laboratories and can be readily automated.

The above discussion provides a factual basis for the detecting, via a solid-phase assay (either competitive on non-competitive) without antibodies, the amount of biological activity and/or quantity of a biologically active substance and/or its inhibitor(s) and kits thereof. The methods used with and the utility of the present invention can be shown by the following non-limiting examples and accompanying figures.

EXAMPLES

General Methods

See Stites et al, Basic and Clinical Immunology, 8th edition, Appleton & Lange for assay technology and general techniques. See also Kemeny and Challacombe, "ELISA and Other Solid Phase Immunoassays, Theoretical and Practical Aspects". J. Wiley and Sons Ltd. New York, N.Y. 1988.

Example 1

ELSA for β-Glucanase and Xylase Activity

Materials. The following materials were obtained from Megazyme Pty.Ltd. Sydney, N. S. W., 2102, Australia: lichenase (endo-1,3-1,4-β-D-glucan-4-glucanohydrolase, EC 3.2.1.73) from *Bacillus subtilis* (batch MLI 82001), exo-1,3-β-glucanase (EC 3.2.1.58) from Trichoderma sp. (EBG 00703), barley β-glucan (lot BBG 30108), rye flour arabinoxylan (pentosan, batch MRP 90801), xylanase (endo-1,4-β-D xylan xylanohydrolase, EC 3.2.1.32) from Trichoderma viride (batch MXY 80202) and azo-barley glucan. Cellulase (1,4-β-D-glucan-4-glucanohydrolase, EC 3.2.1.4) from *Aspergillus niger* (Type 2), Pullulanase (limited dextranase, amylopectin 6-glycohydrolase, EC 3.2.1.41) from *Enterobacter aerogenes*, α-amylase (1,4-D glucan glucanohydrolase, EC 3.2.1.1) from porcine pancreas (Type 1-A), biotinyl-N-hydroxysuccinimide-esters (BNHS), ethylenediamine, p-nitrophenyl phosphate, diethanolamine and Tween-20 were from Sigma Chemical Co., St. Louis, Mo. Sodium periodate and sodium borohydride were from Fisher Scientific Co. Fairlawn, N.J.; alkaline phosphate-streptavidin from Zymed laboratories, Inc., San Francisco, Calif.; microtiter plates (Falcon 3911, Microtest III) from Becton Dickinson Labware, Oxnard, Calif.; dimethyl sulfoxide (DMSO) from J. T. Baker Chemical Co., Phillipsburg, N.J. 08865; and instant skim milk powder was from Nestle, 1185 Englinton E. Don Mills, Ontario. RM-1 was a crude enzyme preparation from Finnfeeds International Ltd and contained high β-glucanase, xylanase and other enzyme activities. All solvents and reagents were of analytical grade.

Preparation of biotin-glucan conjugates. The technique is based on the principle that active aldehyde groups which is generated after sodium periodate oxidation of the hydroxyl group of the polysaccharide moiety, reacts with ethylenediamine to form an aminated polysaccharide. The Schiff bases that are formed are stabilized by reaction with sodium borohydride (Wong, 1991). The amine groups can then be conjugated to biotin using BNHS. In brief, 75 mg β-glucan was dissolved in 2 mL distilled water and 0.1 mL of 100 mM $NaIO_4$ was then added. The reaction was protected from light and mixed for 0.5 hours at room temperature. The reaction mixture was treated with 1 mL ethylenediamine for 2 hours and unreacted reagents were removed by ethanol precipitation. This involved the addition of 8 mL of 95% (V/V) ethanol to the reaction mixture (3 mL), followed by mixing of the sample, centrifugation at 10000 g for 10 minutes at 0° C. and dissolving the pellet in 2 mL of distilled water. The preparations was washed three times. The washed precipitate was then dissolved in 2 mL distilled water, 5 mg of sodium borohydride were added and the reaction was allowed to proceed for 4 hours at 4° C. The washing steps as indicated above were repeated three times. The biotin ester (BNHS, 15 mg or 0.15 mg) was dissolved in 0.2 mL DMSO, the mixture was allowed to react at room temperature for 3 hours followed by three ethanol precipitations as described above. The final precipitate was dissolved in 3 mL distilled water, divided into aliquots and each aliquot of the BNHS-β-glucan complex was store frozen at 0° C. in sealed polypropylene containers. The ratio of BNHS to β-glucan were 0.2 and 0.002 for the complexes that were synthesized from 15 mg or 0.15 mg BNHS and 75 mg β-glucan, respectively.

Buffers and coating of plates. Phosphate-buffered saline [PBS, NaCl 4.39, $Na_2HPO_4$ 8.19 and $NaH_2PO_4$ 2.45 (g/L); pH 7.2] containing 0.3% (W/V) skim milk was used for dilution of the alkaline phosphate-streptavidin complex. The wash buffer for the titer plates was PBS (pH 7.2) containing 0.05% (V/V) Tween 20 (PBS-T). Sodium phosphate buffer (20 mM, pH 6.5) was used for the dilution of all enzyme preparations except for xylanase which was diluted in 25 mM acetate buffer (pH 4.7). Alkaline phosphate substrate solution contained 1 mg/ml of p-nitrophenyl phosphate in 1 M diethanolamine buffer (pH 9.8).

The microtitre plates were directly coated with 0.1 mL/well of the biotin-glucan complex diluted in 0.05 M carbonate-bicarbonate buffer (pH=9.6), and then left at room temperature for 1 hr and overnight at 40° C. The usual dilutions of the 0.2 and 0.002 stock biotin-glucan complex were 50,000 and 100 fold, respectively. The plates were washed 3 times with PBS-T buffer and the emptied plates were stored in sealed containers at 0° C. for up to several months.

Test procedures. β-Glucanase (lichenase) was diluted with 20 mM sodium phosphate buffer (pH 6.5) to the desired concentration. The enzyme (100 μL) was added to each well in the biotin-glucan coated microtiter plate, the plate was sealed with a low evaporation lid, and the mixture was incubated for the desired period of time (from 1 to 30 minutes) and at the desired temperature (usually 22–24° C.). The reaction was stopped by emptying the plates followed by washing of the wells three times with pH 7.2 PBS-T. Blanks contained the incubation buffer without enzyme. Alkaline phosphatase-streptavidin (100 μg) diluted 1:1000 in pH 7.2 PBS was added to each well and incubated for 30 minutes at room temperature. The plates were washed six times with pH 7.2 PBS-T and dried at ambient temperature for approximately 10 to 20 minutes. Alkaline phosphatase substrate solution was then added to each well (100 μL) and the microtiter plates were incubated at room temperature for 30 minutes, or until absorbency of the well with no enzyme yielded a value of from 1.5 to 2.0 optical density units. The plates were read at 405 nm using a microtiter plate reader (Bio-Rad Laboratories Ltd., Mississauga, ON, Canada, Model 450).

Other procedures The method for preparing the arabinoxylan substrate was the same as used for β-glucan except the substrate was arabinoxylan rather than β-glucan. The BNHS to arabinoxylan ratio was 0.2 with the stock substrate being diluted 10,000 fold prior to being coated on the plate. The azo-barley-glucan method for the assay of β-glucanase was according to the procedure described by McCleary and Shameer (1987). The precision of the assay was studied using three concentration of enzyme (0.076, 2.1 and 160 mU)/well. They were added (100 μl) to wells containing the 0.2 biotin-β-glucan diluted 1 to 50,000 and the mixture was incubated for 15 minutes at 22° C. Other procedures were as described above. The assay within the same titer plate was replicated 8 times. The entire assay was replicated 6 times. In the study on the effects that β-glucan had on enzyme activity, β-glucan (5.12 mg/mL) in 20 mM sodium phosphate buffer (pH6.5) was mixed with an equal volume of 0.2 U/mL of β-glucanase and hydrolysed at 40° C. for 60 minutes. The reaction was stopped by putting the enzyme solution in a boiling water bath for 15 minutes. The control sample contained β-glucan but was not incubated with enzyme and was not subjected to boiling. The hydrolysed β-glucan and nonhydrolyzed solutions were added to wells (50 μl) containing 0.2 biotin-glucan (1 to 50,000 dilution) and the solution was incubated with 50 μl of β-glucanase (0.5 mU). The reaction was completed after incubation at 22° C. for 15 minutes. Other conditions were as described above.

Results and Discussion

Figure 3:
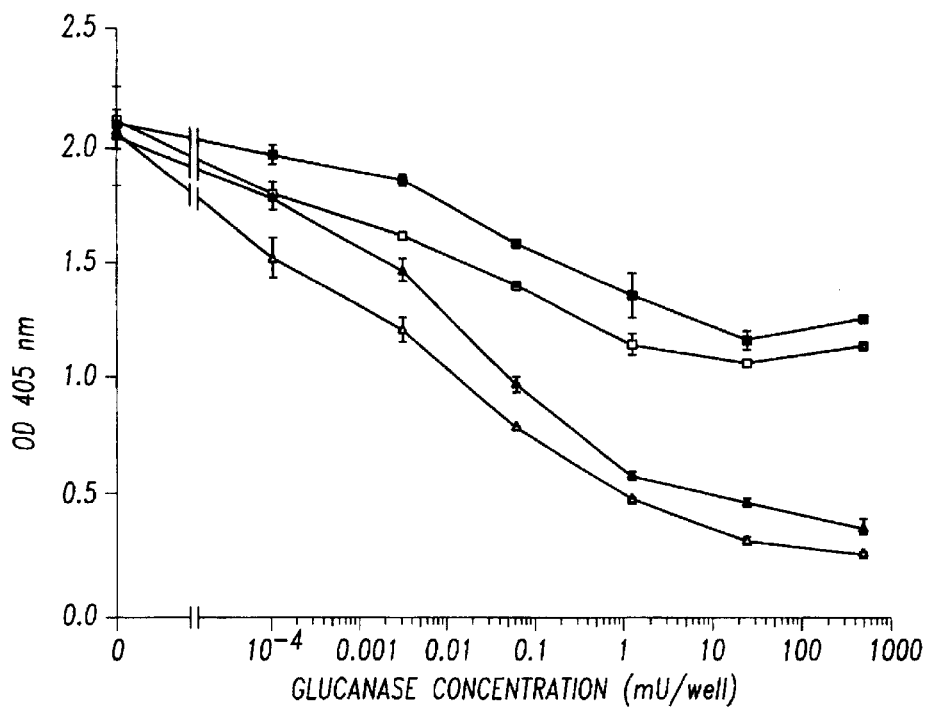
FIG. 3 is a graph of the hydrolysis of biotin-glucan substrates by β-glucanase (lichenase) followed by the quantitation of unhydrolysed β-glucan using a second enzyme. Two concentrations each of the 0.002 biotin-glucan complex [1 to 50 (■) and 1 to 100 (□) dilutions] and of the 0.2 biotin-glucan complex [1 to 50,000 (♥) and 1 to 100,000 (Δ) dilutions] were coated onto titer plates and prepared as described in Material and Methods (Example 1). β-Glucanase (100 μl) was added to the wells at the concentrations indicated and the mixtures were incubated at 22° C. for 15 minutes. The reaction was stopped by washing with PBS-T and phosphatase-streptavidin was added to each wells followed by washing to remove the unbounded complex. The amount of bounded phosphatase was quantitated enzymatically following incubation with p-nitrophenyl phosphate in 1 M diethanolamine buffer for 30 minutes at 22° C. Values represent mean±SD of triplicate analysis.

Hydrolysis of β-glucan. The optical density change obtained by the hydrolysis of different biotin-glucan substrates in the presence of different concentration of β-glucanase followed by the detection of the unhydrolyzed substrate using an alkaline phosphatase-streptavidin complex is shown in FIG. 3. The absorbency values provides a measure of the amount of substrate that was not hydrolysed. The net amount of substrate hydrolysed can therefore be estimated by subtracting the absorbency value in absence of enzyme from those obtained for the individual assays.

The labelling of glucans at a biotin/glucan ratio of 0.2 (w/w) gave a steeper standard curve with larger absorbency changes than the values obtained with the complex that had a 0.002 ratio. Also the higher dilution of substrate with either degree of biotinylation yielded assays that were more sensitive. These results suggest that increased sensitivity of the assay with lower background values can be achieved by increasing the biotin/glucan ratio of the substrate and by using a more dilute solution of the substrate to coat the plate. There are limitations, however, to the degree that this can be carried out as excessive biotinylation of the substrate may reduce its accessibility to the enzyme. Similarly, although, higher dilutions of the substrate increases the sensitivity of the assay they also cause a near proportionate increase in the time required for color development. Clearly a compromise needs to be made in the degree of binding of biotin to the substrate and the corresponding dilutions of the substrate that are used as these affect the sensitivity of the assay, background values and the time required to achieve a suitable color reaction. The 0.2 biotin-glucan substrate at a dilution of 100,000 was able to detect β-glucanase activity in the range of from 1 to 100 mU/well. These data suggest that the assay is able to detect very low enzyme activity values.

Figure 4:
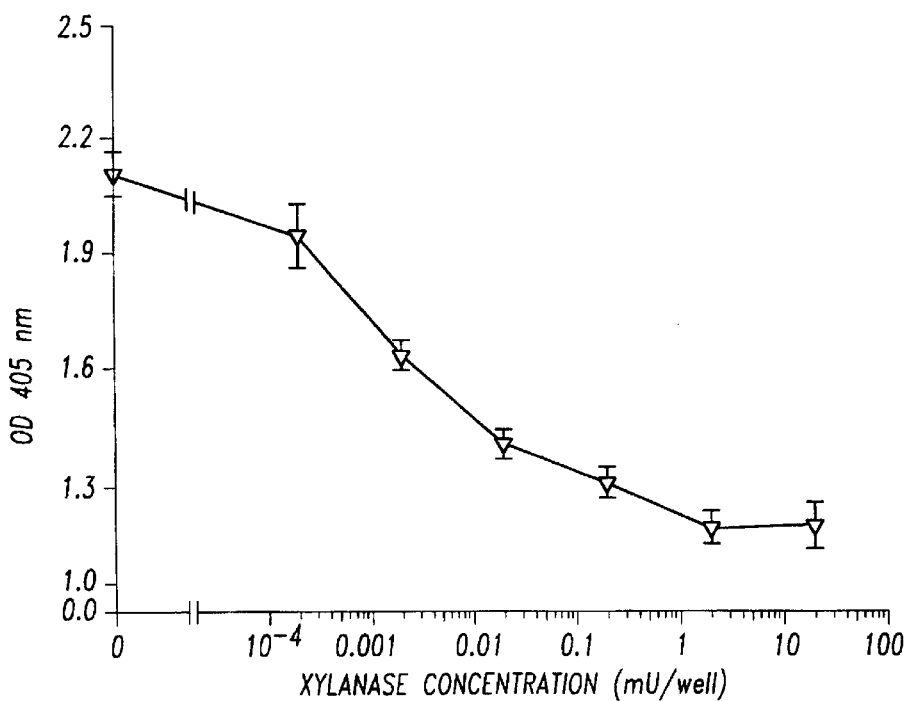
FIG. 4 is a graph of the standard curve for the xylanase assay. The biotin (BNHS) to arabinoxylan ratio was 0.2 with the dilution of the substrate being 1 to 10,000. The amount of enzyme added to each well is indicated on the abscissa. Other conditions were as described in FIG. 3 and in Materials and Methods (Example 1). Values represent mean±SD of triplicate analysis.

A similar curve to that obtain with β-glucanase was obtained with xylanase when the substrate was a biotin-arabinoxylan complex (FIG. 4). No activity was obtained with this assay when β-glucanase was added to the incubation mixture.

Figure 5:
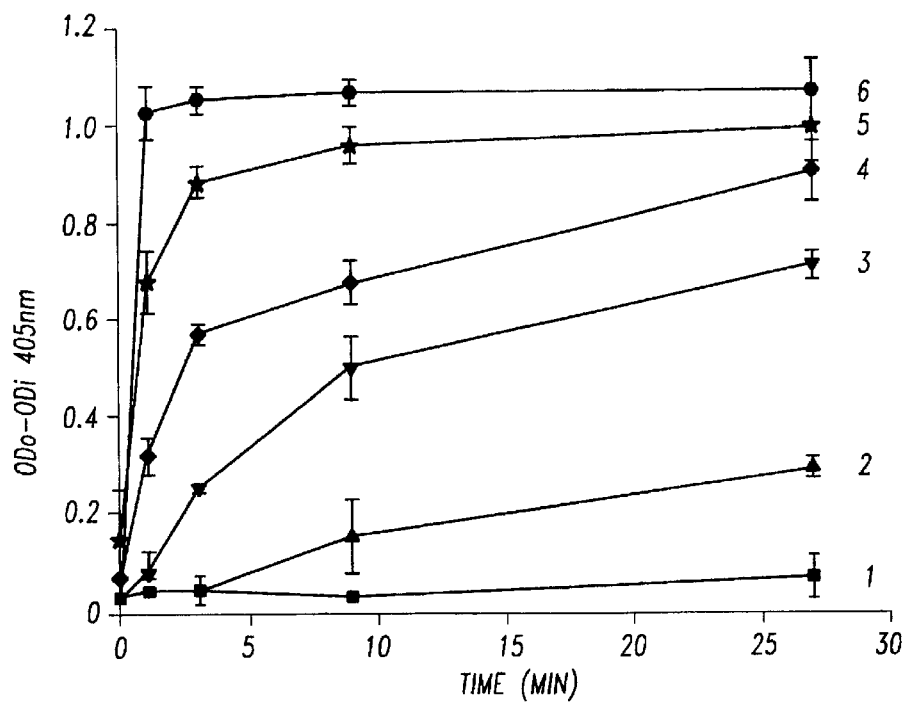
FIG. 5 is a graph of the time course for the hydrolysis of biotin-β-glucanase (lichenase). The enzyme was incubated for 0, 1, 3, 9, 27 min at 22° C. with the dilution of the 0.2 biotin-glucan being 1 to 50,000. The six concentrations of enzymes were: 0.032 (1), 0.16 (2), 0.8 (3), 4 (4), 20 (5) and 100 (6) mU/well. The color development time was 30 minutes at 220° C. Other procedures were as described in Materials and Methods (Example 1) and FIG. 3. The net β-glucanase activity was obtained by subtracting the absorbency values obtained in the absence of enzyme (ODo) from those containing enzymes (ODi).
Figure 6:
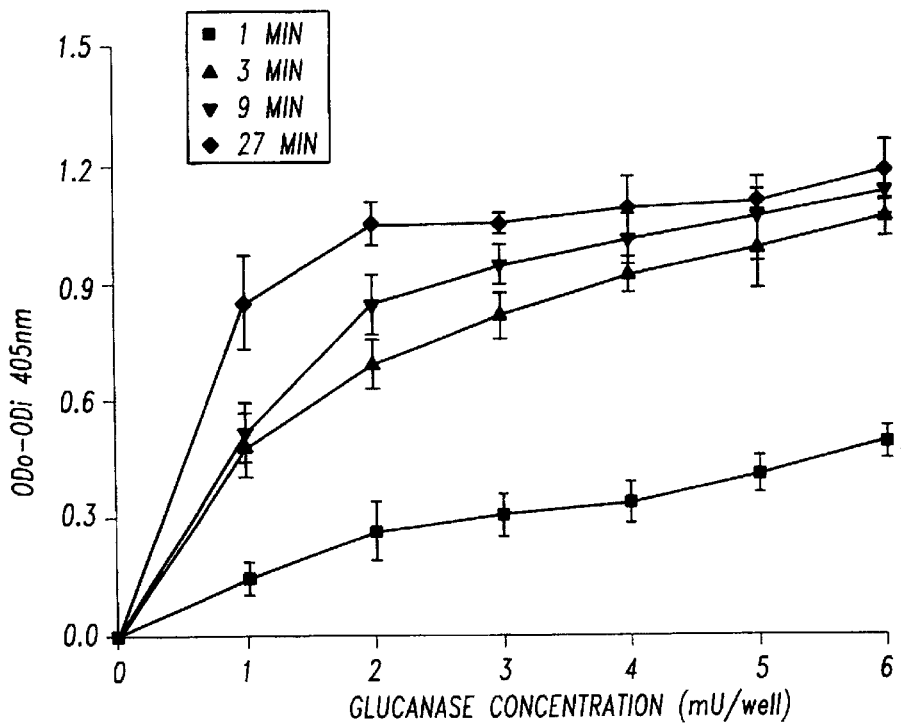
FIG. 6 is a graph of the influence of β-glucanase (lichenase) concentrations on the hydrolysis of biotin-glucan. Assay times and enzyme concentration are indicated in the Figure. Other conditions were as described for FIG. 5.

Time course response at different enzyme concentrations. In this study the biotin-glucan complex was hydrolysed in the presence of from 0.032 to 100 mU/well of β-glucanase over a time period of from 1 to 27 min (FIG. 5). In this and subsequent assays the net absorbency values due to enzyme activity were plotted ($OD_1$—$OD_1$ at 450 nm). The results demonstrate that at the high concentration of enzyme (100 mU/well) the reaction is complete within one minute whereas at the low concentration (0.032 mU/well) the reaction rate was low and remained linear over a period of 27 minutes. The results shown in FIG. 6 demonstrate that there was a near linear increase in the rate of reaction with increasing amounts of enzyme during a short incubation period (1 and 3 minutes) and that the curve became progressively less linear with increasing amount of enzyme as the incubation times were increased. These results indicate the amount of β-glucanase in a sample can be estimated provided proper assay conditions are selected. The advantage of the assay in addition to being highly sensitive is that as many as 200 assays can be completed by one person in a single day. A disadvantage of this assay is that it provides a measure of the relative rather than the absolute units of enzyme activity. The procedure, however, can be calibrated against an enzyme of known activity in a manner similar to that used with the azo-barley glucan assay (McCleary and Shameer, 1987). Use of such a calibration or standard curve therefore provides a more absolute value.

Figure 7:
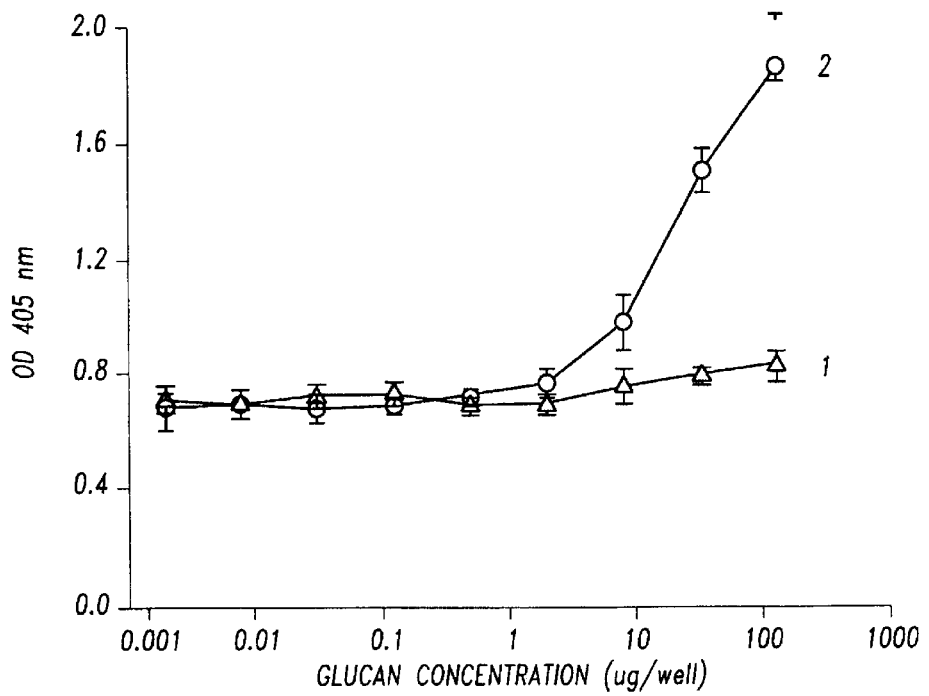
FIG. 7 is a graph of the influence of prehydrolysed (Δ) and unhydrolysed (○) β-glucan on β-glucanase (lichenase) activity. Different amounts of the two forms of β-glucan as shown in the figure were added to wells containing bound biotin-β-glucan followed by the addition of 0.5 mU of β-glucanase/well (50 μL). Other conditions were as described in Materials and Methods (Example 1) or FIG. 5.

Influence of exogenous β-glucan on assay values. It is well known that β-glucanase as well as other carbohydrate hydrolysing enzymes are bound to their substrate (Headon, 1993; Yu et al., 1995) and that this interferes with this assay when the exogenous substrate is present in the sample at high concentrations. The current study demonstrated that the presence of the hydrolysed substrates did not affect the results whereas there was a reduced activity of the enzyme, as seen by the absorbency changes, when the amount of β-glucan in the well exceeded 1 μg/well (FIG. 7); this would be equivalent to 10 μg/mL of β-glucan in an extract containing the enzyme. Barley that contain a high concentration of β-glucan (i.e., 5%) when extracted with a near minimum amount of buffer (assume a 1 to 10 weight to volume ratio) would therefore contain 5 μg β-glucan/mL. Under such conditions, the β-glucans in the extract would have only a minimal effect on β-glucanase activity. However, if there is a suppression of β-glucanase activity by exogenous β-glucans, its effects can be reduced by prior enzymatic hydrolysis of the extracted β-glucans in a manner analogous to that shown for FIG. 7. The presence of endogenous substrate with the other β-glucanase assays, as discussed herein below, have a higher probability of yielding low assay values as the dilution of the enzyme extract with these assays, due to reduced sensitivity of the assay, would be much less than that used in the current study.

The data from this study, also, show that a modified form of the assay can be used to quantitate the amount of β-glucan in an extract. Under such conditions a competitive ELSA will utilize two forms of substrate; the unknown amount in the extract and the reference amount or the biotinylated β-glucan which would be bound to the surface of the well. Such an assay is analogous to an ELISA which is widely used for the detection of low molecular weight analyses (Kemeny and Challacombe, 1988).

Precision of assay. The within-assay mean±SD for the ELSA, as assessed by eight repeated analyses of three concentrations of enzyme (160, 2.1 and 0.076 mU/mL), yielded absorbency values of 0.33±0.016 (CV=6.4%) and 1.25±0.06 (CV=4.9%) and 1.92±0.078 (CV=4.0%), respectively. There were greater variation in absorbency values between runs (average CV=12.9%) than within runs (average CV=5.1%). Differences in incubating and color development times, ambient temperature, or other variables could have contributed to the between-run variation. This is reduced by the use of appropriate reference standards and by the more rigid control of assay conditions.

Figure 8:
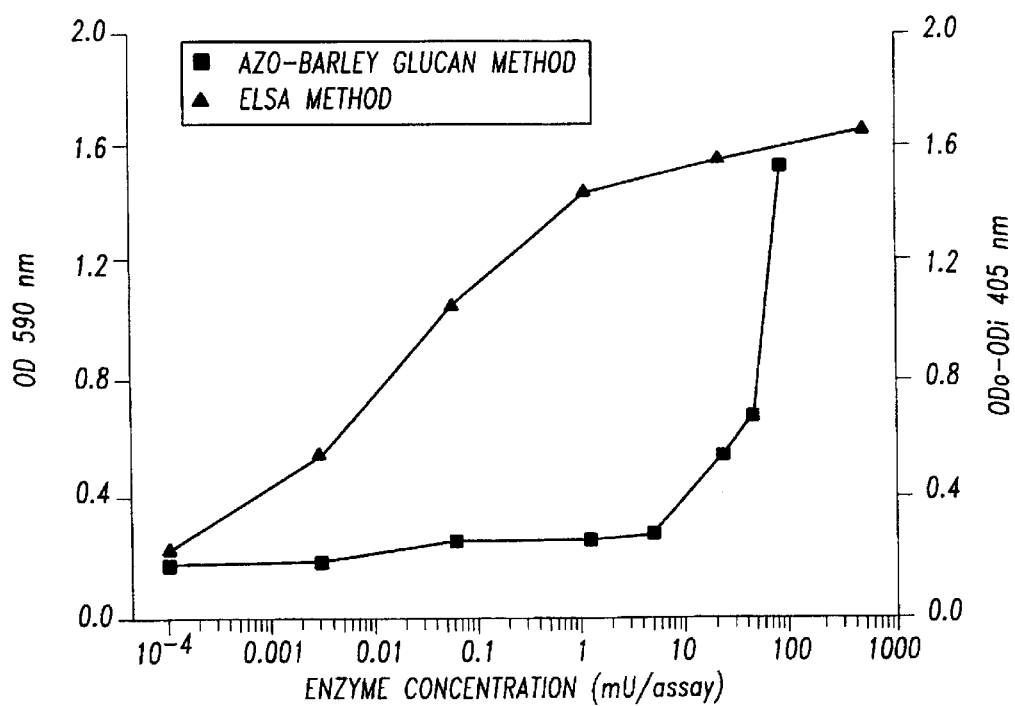
FIG. 8 is a graph of the standard curves comparing the azo-barley glucan and ELSA methods for β-glucanase (lichenase): ELSA (■), azo-barley glucan (▲). See Materials and Methods (Example 1) and FIG. 5 for details of the two assays.

Relationship between the azo-barley-glucan method and the ELSA for the assay of β-glucanase activity. The objective of this study was to compare the sensitivity of the assay as developed in this study with another indirect and very popular assay, the azo-barley β-glucan method (McCleary and Shameer, 1987). In this comparison the concentration of enzyme was plotted on a logarithmic scale so as to compare the sensitivity of the two assays over a wide range of activities. As indicated in FIG. 8 the azo-dye procedure gave a steep response at a relatively high concentration of the enzyme whereas the ELSA produced a more gradual responses but was much more sensitive. The detection range for the ELSA was from 0.001 to 1 mU/assay; whereas that of the azo-barley glucan procedure was from 10 to 100 mU/assay, a difference in sensitivity of from 10 to 100,000 fold. The azo-blue dye also has limitations as the method, which is considerably more simple than other standard methods, requires a precipitation step followed by a centrifugation step to separate the hydrolysed and unhydrolysed substrate. These step precludes the adaptation of the procedure to the formate that is used for the ELSA. The azo-dye method must also be standardized since it suffers from changes in parameters such as the solubility of the dyed polysaccharide fragments as influenced by factors such as the ionic strength of the precipitant, the temperature of precipitation and the centrifugation conditions. These data suggest for the assay of β-glucanase activity using the ELSA is much easier to carry out and is considerably more sensitive than the corresponding azo-barley glucan method.

Hydrolysis of biotinylated-β-glucan by other enzymes. Results shown in Table 1 compare the degree of hydrolyses of biotinylated-β-glucan by different enzyme preparations. In all of these assays the enzyme was diluted to a common activity based on assay values provided by the producer of the enzyme; as a result, the comparisons are not precise but only approximate. The results, nevertheless, demonstrate that those enzymes that are capable of hydrolysing β-glucan such as lichenase, (the reference enzyme), and cellulase (McClear and Glennie-Holmee, 1985) are able to hydrolyse biotinylated-β-glucan. RM-1, a crude enzyme preparation high in β-glucanase activity, was also able to hydrolyse the biotinylated β-glucan. Other enzymes with a low ability to hydrolyse β-glucan such as exo-1,3-β-D-glucanase (Wood and Bhat, 1988) or no ability to hydrolyse the substrate (i.e., Pullualnase, β-xylanase and α-amylase) also yielded low values relative to those obtained with lichenase. The activity associated with α-amylase may be due to the presence of some contaminating starch in the β-glucan preparation or possibly to residual β-glucanase activity in the enzyme preparation. The ability of cellulase to hydrolyse the substrate also suggests that a modification of the substrate (i.e., use of cellulose rather than β-glucan) would provide a basis for its assay.

Example 2

Quantitating Enzyme and its Inhibitor

This Example provides for quantitating the amount of enzyme in a sample but also for quantitating the concentration of its inhibitor. The assay, which is referred to as a biotinylated enzyme inhibitorsorbent assay (BEISA), is based on the specific binding of a biotin-labelled enzyme with its corresponding inhibitor.

Methods: NHS-biotin solution (5.5 mg in 200 ul dimethyl sulfoxide) and trypsin solution (15 mg in 1000 ul PBS) were mixed and reacted at room temperature for 3 hours with gently shaking. The unconjugated biotin was removed at 4° C. using minicon-15 concentrator (Amicon. Co.). The final volume was 1000 ul.

All chemicals were from Sigma chemical Co., St Louis, Mo. or Fisher Scientific Co., Winnipeg, MB. Trypsin (EC 3.4.21.4) and its inhibitors, ovomucoid from egg white and leupeptin, were used as a model to demonstrate the BEISA.

The 96-well microtiter plate (Falcon 3911) was coated with trypsin egg white inhibitor (ovomucoid, 4 ug/100 ul/well) at 370° C. overnight. The plate was washed once using PBST {[PBS, NaCl, 9.00; Na$_2$HPO$_4$, 1.15; NaH$_2$PO$_4$, 0.23 (g/l) pH 7.2] plus 0.05% Tween-20} and 200 ul of 5% skim milk was added to each well of the plate followed by incubation at 37° C. for 2 hours. The plate was rinsed twice with PBST and 50 ul of PBS was added to each well of the plate except for those in column one where 100 ul of PBS was added. Unlabelled trypsin (50 ul of 400 ug/ml) was added to the wells of the second column followed by successive double dilutions of trypsin in wells up to and including those in column 11. Biotinylated trypsin in PBS (50 ul of 1:3000 dilution of the stock to yield approximately 2 ug/100 ul/well) was added to each well except those in the first column followed by incubation at 37° C. for 1 hour. The final volume in each well was 100 ul. The blank set of wells with no trypsin (column 1) served as the negative control while the last set of wells (column 12) with biotinylated trypsin but no unlabelled trypsin served as the positive control. The plate was then washed three times with PBST and 100 ul of streptavidin-alkaline phosphatase (1:1000 in 50 mM bicarbonate buffer, pH 9.5) was added to each well of the plate and the plate was incubated at room temperature for 30 minutes. The plate was washed five times using PBST and 100 ul/well of p-nitrophenyl phosphate substrate (1 mg/ml in 10% diethanolamine buffer, pH 9.8) was added to the plate followed by incubation at ambient temperature for about 30 minutes. The absorbency was then read at 405 nm using a microplate reader (Bio-Rad laboratories Inc. Mississauga, ON, Canada, model 450). The values represent a mean of triplicate analysis. The absorbency ±SD of the positive control was 1.9±0.02 optical density (OD) units.

Figure 9:
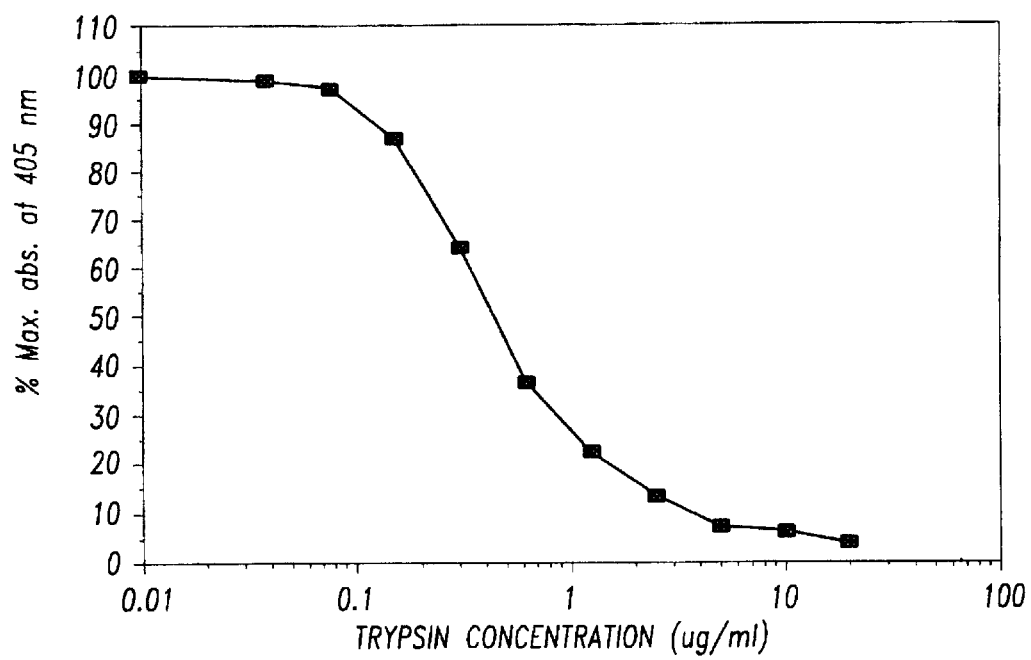
FIG. 9 is a graph of the typical dose-response curve of trypsin concentration (Example 2).
Figure 10A:
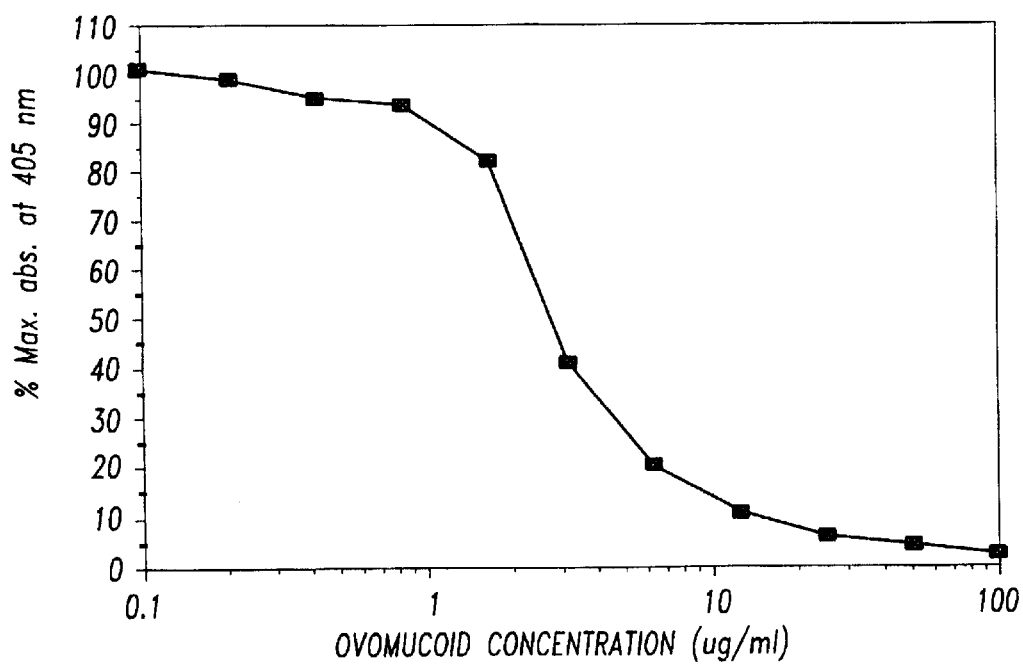
FIGS. 10A–B are graphs of dose-response curve for the determination of the concentration of ovomucoid (A) or leupeptin (B). The assay procedure was the same as that for FIG. 9 except the ovomucoid (A) or leupeptin (B) replaced unlabelled trypsin as the variable competitor. The values represent a mean of triplicate analysis. The absorbencies ±SD of the positive controls were 2.0±0.01 (A) and 1.95±0.002 optical density (OD) units.
Figure 10B:
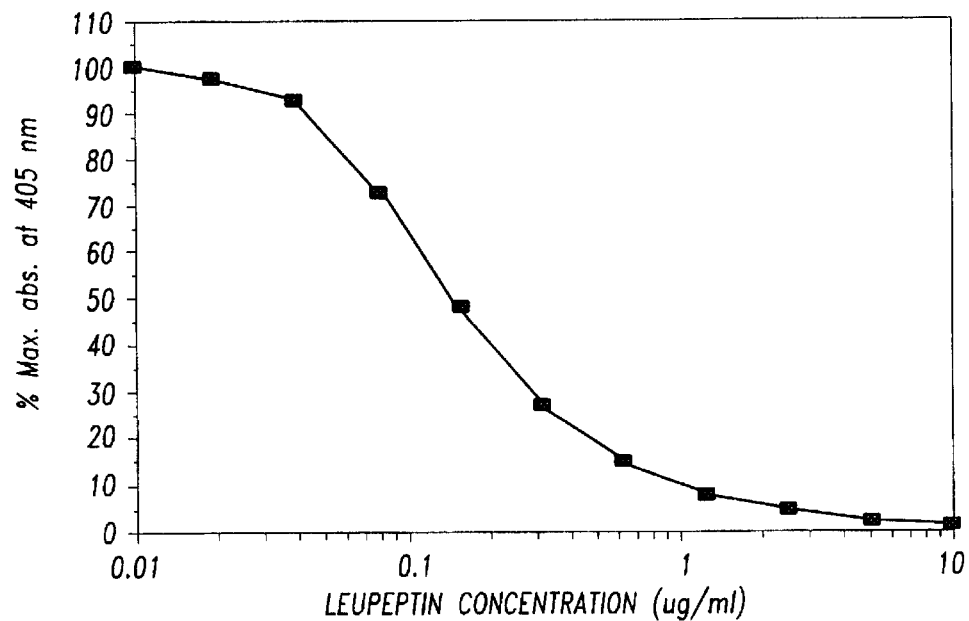

The concentration of trypsin that could be detected was from 0.1 to 1.0 ug/ml (FIG. 9) while the concentration of the inhibitors that could be detected ranged from 1 to 10 ug/ml for ovomucoid (FIG. 10A) and from 0.03 to 1 ug/ml for leupeptin (FIG. 10B). The sensitivity of the assay can be increased by decreasing the amount of ovomucoid that is coated onto the well of microtiter plate. Under such conditions a longer incubation period is required with the color producing enzyme. Modification of the color developing assay through the use of avidin coupled with multiple units of alkaline phosphatase can result in a proportional decrease in time required for the color producing step.

Figure 11:
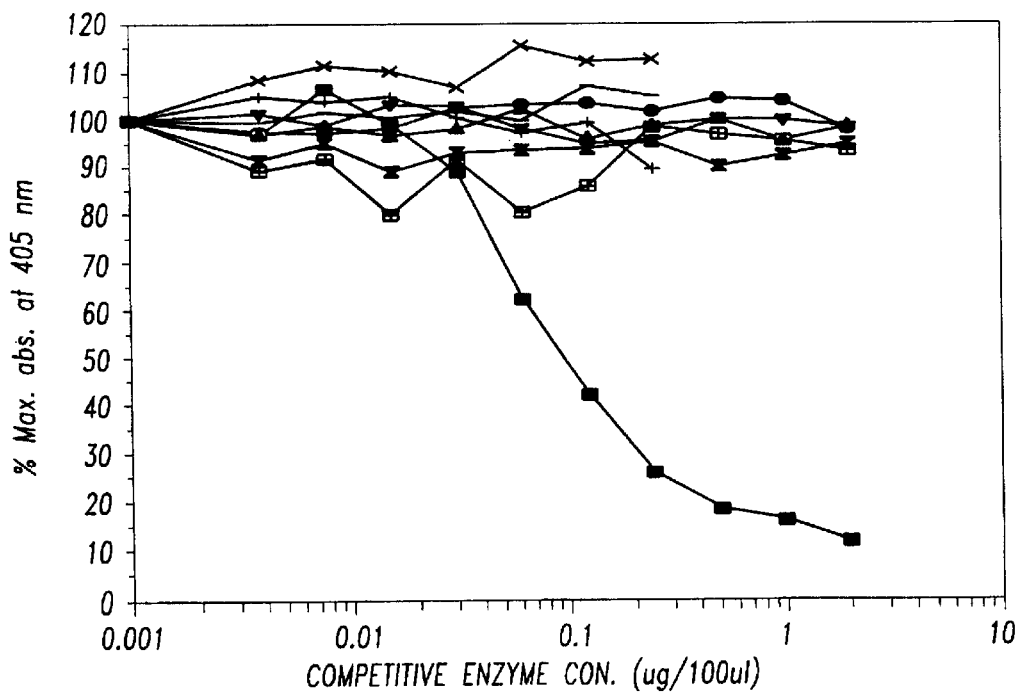
FIG. 11 is a graph of the cross-reactivity of trypsin egg white inhibitor (ovomucoid) with different proteases. The proteases used in this experiment were trypsin (EC 3.4.21.4), ■—■; collagenase (EC 3.4.24.3), ▽—▽; cathepsin D (EC 3.4.23.5), ●—●; elastase (EC 3.4.21.11), Δ—Δ; thermolysin (EC 3.4.24.27), __—__; pepsin (EC 3.4.23.1), |—|; papain (EC 3.4.22.2), __—__; protease XIII (EC 3.4.23.18), -——-; protease XXXI, +—+; and protease IV, ⊠—⊠. The assay procedure was the identical to that given in FIG. 9 except the other proteases replaced unlabelled trypsin as the variable competitor. The values represent a mean of triplicate analysis. The absorbency ±SD of the positive control was 1.85±0.007 optical density (OD) units.

The specificity of BEISA for a particular enzyme depends on the specificity of inhibitor chosen for coating the microplate. In this assay, there was no cross reactivity of trypsin egg white inhibitor (ovomucoid) with other proteases (FIG. 11). These results, therefore, show that the BEISA can be used to specifically quantitate trypsin in the presence of other proteases. In addition another inhibitor that is known to bind elastase, elastatinal, did not interfere with the binding of labelled trypsin to trypsin inhibitor. Likewise, other protein such as bovine serum albumin (BSA), human serum albumin (HSA) and α-casein did not interfere with the assay.

The BEISA is a new method that can be used to quantitate trypsin and trypsin inhibitor. The method is sensitive, specific, simple to use and can be adapted to high throughput screening and automation. Sample cleanup should not be required as all compounds that would interfere with the color development step would be eliminated in the washing steps. The procedure can be applied to any enzyme that has an appropriate inhibitor. There are 8000 inhibitors are known to react with about 2000 enzymes (Zollner, 1993).

Although, the procedure in this assay involved the coating of the inhibitor to the surface of a microtitre plate and the labelling of the enzyme with biotin the opposite procedure can also be carried out, that is, the enzyme can be coated on the surface of the plate and the inhibitor can be labelled with biotin.

Example 3

Solid Phase Assay for Protease and Protease Inhibitors Using Biotinylated Casein Materials: α-casein, biotinamidocaproate n-hydroxysuccinimide ester (NHS-biotin), Tween-20, p-nitrophenyl phosphate disodium (pNPP), trypsin (EC 3.4.21.4), papain (EC 3.4.22.2), thermolysin (EC 3.4.24.3), collagenase (EC 3.4.24.3), pepsin (EC 3.4. 23.1), cathepsin D (EC 3.4.23.5), elastase (EC 3.4.21.11), protease IV (*Streptomyces caespitosus*), protease XXXI (*Bacillus licheniformis*) and protease XIII (*Aspergillus saitoi*) (EC 3.4.23.18) and ovomucoid were from Sigma chemicals Co., dimethyl sulfoxide (DMSO) from J. T. Baker chemical Co., and microtitre plates (Falcon 3911) from Becton Dickinson and Co. Citrate (0.1M)-phosphate (0.2M) buffers (Stoll et al., 1990) were used for papain (pH 6.2), protease XIII (pH 2.8), cathepsin D (pH 3.0), elastase (pH 6.5); phosphate (0.2 M) buffers (Stoll et al., 1990) for trypsin (pH 7.5), protease IV (pH 7.5), protease XXXI (pH 7.5), thermolysin (pH 7.5) and collagenase (pH 7.1); while 10 mM HCl was used for pepsin (pH 2.0).

Preparation of biotinylated casein: 12 mg α-casein in 1 ml of 0.1 M pH 7.2 phosphate-buffer saline [PBS, NaCl, 9.00; Na$_2$HPO$_4$, 1.15; NaH$_2$PO$_4$, 0.23 (g/l)] was allowed to react with 3.6 mg NHS-biotin in 150 ul DMSO for 2 hours at room temperature with gently shaking.

Figure 12:
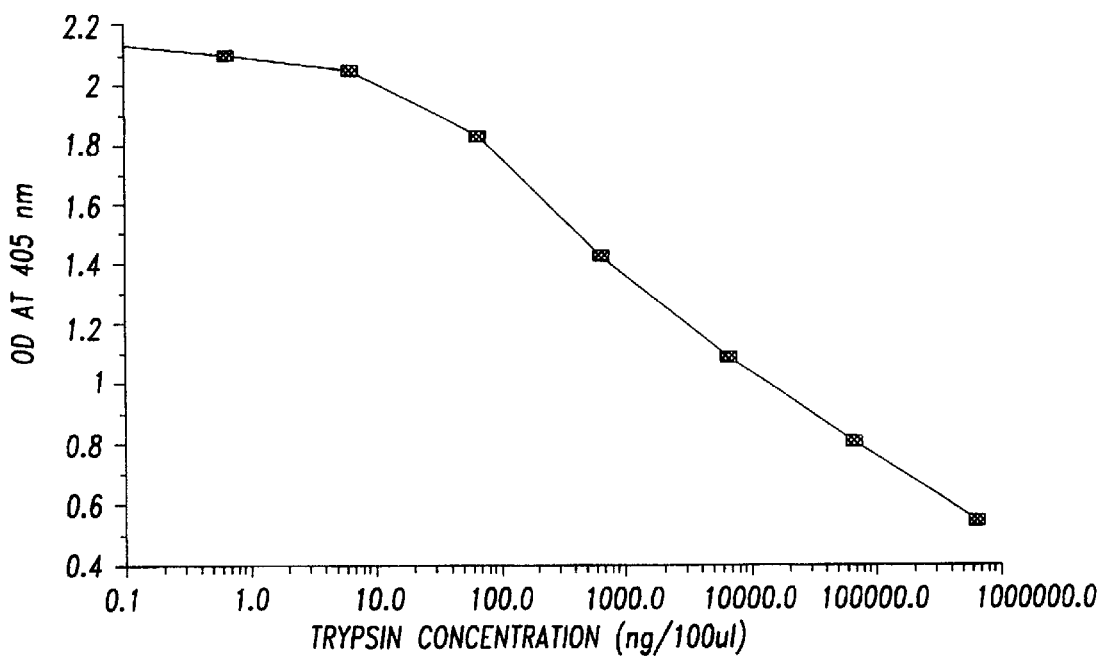
FIG. 12 is a graph of the hydrolysis of biotinylated α-casein by trypsin. The values represent the mean of triplicate analysis with the mean SD being ±0.005OD units. (See Materials and Methods Example 3).
Figure 13:
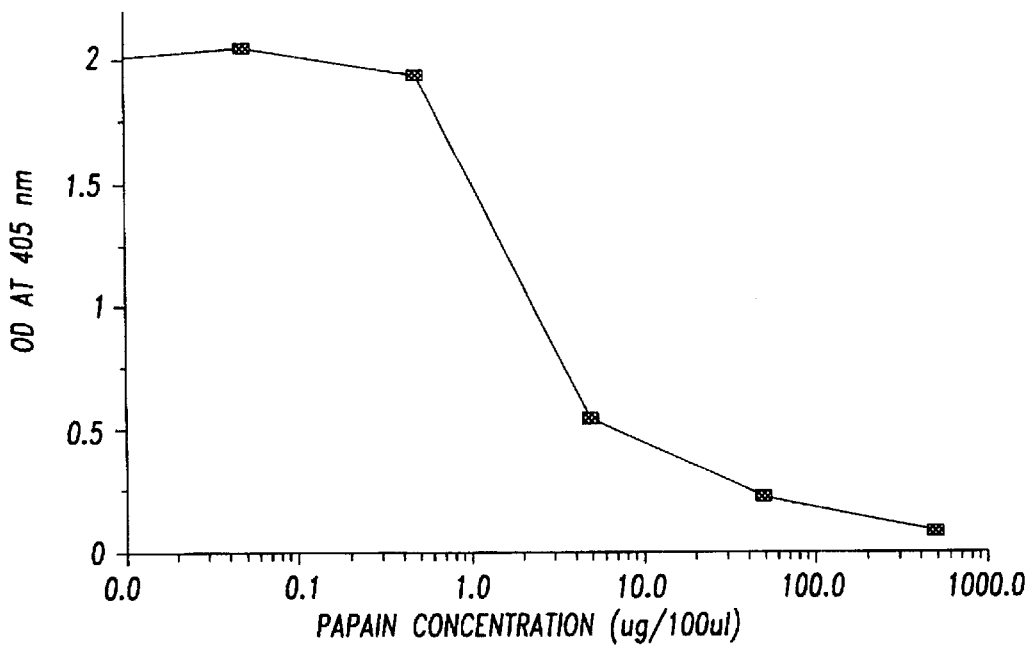
FIG. 13 is a graph of the hydrolysis of biotinylated α-casein by papain. The values represent the mean of triplicate analysis with the mean SD being ±0.005OD units.
Figure 14:
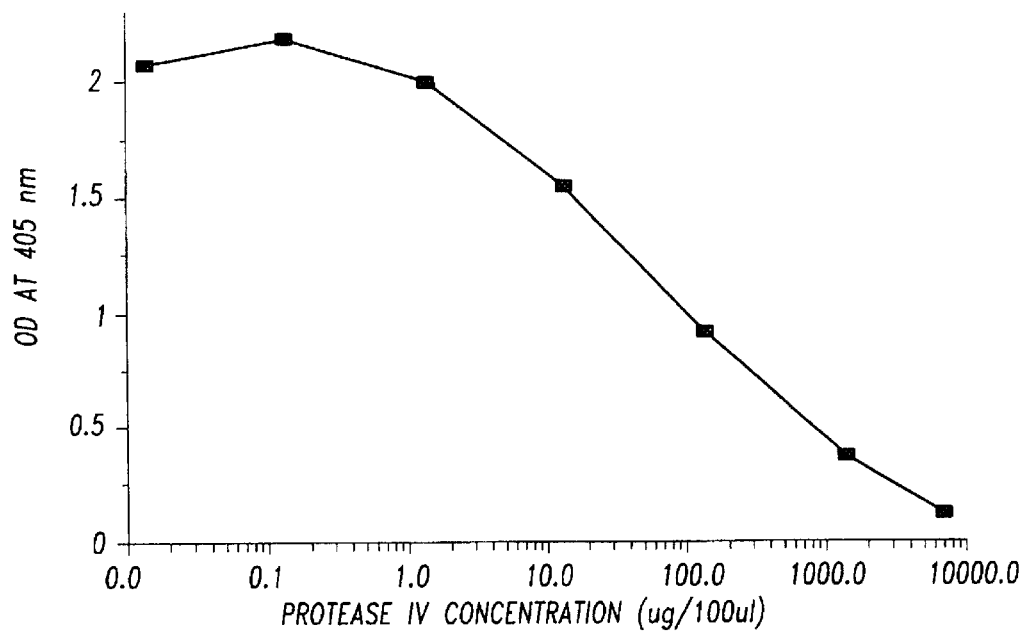
FIG. 14 is a graph of the hydrolysis of biotinylated α-casein by protease IV (*Streptomyces caespitosus*). The values represent the mean of triplicate analysis with the mean SD being ±0.005OD units.

Assay procedure for protease activity using biotinylated casein: The microtitre plates except for the first column of 8 wells were coated using biotinylated α-casein in PBS (0.13 ug/well/100 ul) and incubated for 2 hours at 37° C. The plates were washed three times with 0.1 M PBST (PBS with 0.05% Tween-20). Different concentrations of the enzyme solution as indicated in FIGS. 12–14 (100 ul) were diluted with the appropriate buffer (see Table 2). They were added in triplicate to the wells of a plate followed by incubating in a humid atmosphere at 37° C. for 30 minutes. The plate was washed three times using PBST to terminate the protease reaction. A streptavidin-alkaline phosphatase solution (100 ul/well, 1:1000 dilution in bicarbonate buffer pH 9.5) was added to all wells in the plate except for the first column of 8 wells (as blank) and the plate was incubated at room temperature for 30 minutes. The blank set of wells contained only PBS, no added enzyme and no coating with biotinylated casein. The reaction was stopped by emptying and washing the plate six times with PBST. The pNPP substrate (100 ul/well, 1 mg/ml in 10% diethanolamine buffer pH9.8) was added to each well of the plate followed by incubation at room temperature for about 20 minutes. The absorbency was then read at 405 nm using a microplate reader (Bio-Rad laboratories, Ltd, Mississauga, ON, Canada; model 450). The best sensitivity was obtained when the maximum absorbency was around 2.0 optical density units.

Assay for amount of inhibitor using biotinylated α-casein casein: The procedure was essentially the same as for the protease activity assay except the concentration of protease (trypsin) was the same in all wells (3.36 ug/100 ul/well) while the concentrations of the inhibitor (ovomucoid) was varied (see FIG. 15). In all cases the plate was covered during incubation to prevent evaporation.

Results

The biotinylated α-casein that was bound onto the surface of the wells of a microtitre plate was hydrolysed by different concentrations of trypsin (FIG. 12), papain (FIG. 13) and protease IV (FIG. 14). The concentration of the different enzymes was from 10 to 10$^6$ ng/100 ul/sample for trypsin, from 0.5 to 4 ug/100 ul/sample for papain and from 1 to 1000 ug/100 ul/sample for protease IV. The sensitivity of the assays as determined by the amount of enzyme required to produce a 10% decrease in maximal absorbency were 30, 700, 200 ng/100 ul, respectively, for trypsin, papain and protease IV. Increases in sensitivity more than 10 fold have been achieved by incubation of the protease for 24 hours rather than 0.5 hour. Likewise considerable improvements in sensitivity can be achieved by the coating of smaller amounts of the labelled casein onto the surface of the well. This change, however, resulted in a near proportionate decrease in the rate of color development by the avidin-alkaline phosphatase conjugate.

Table 2 demonstrated that the biotinylated casein can be used as a substrate for all of the proteases used in this study. These enzymes can be grouped into four classes of proteases including those which have activated serine, cysteine, aspartate and metal ion (IUBMB, 1992). The assay as indicated in Table 1 was carried out at the optimal pH of each enzyme.

Figure 15:
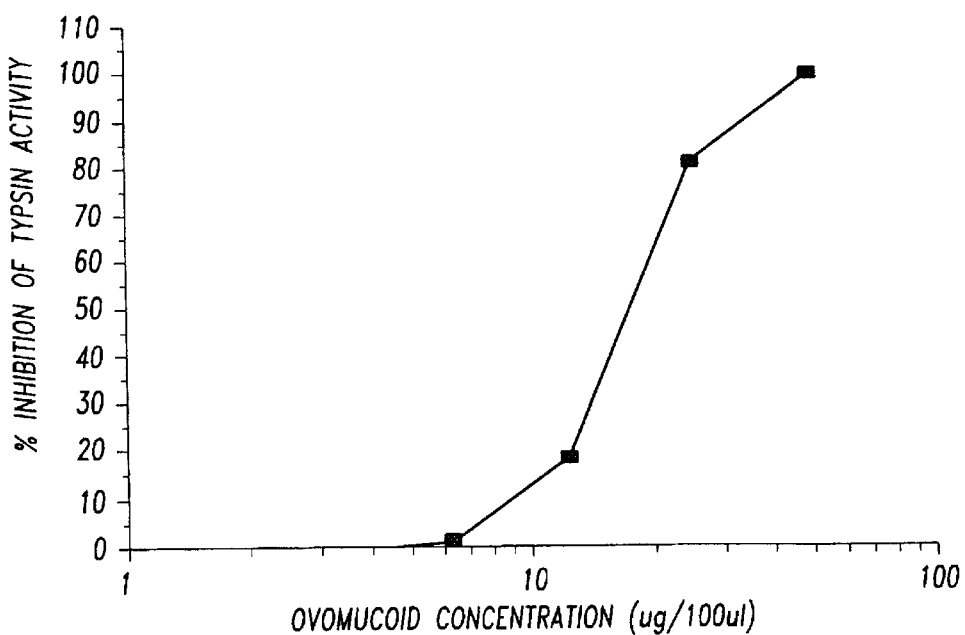
FIG. 15 is a graph of the inhibition of trypsin activity by ovomucoid. The values represent the mean of triplicate analysis with the mean SD being ±0.002OD units. The $OD_{max}$ for 100% of inhibition of trypsin activity was 1.056. $OD_{max}$ is the OD of wells containing both inhibitor and trypsin minus the OD of wells containing only trypsin.

Studies with ovomucoid, a trypsin inhibitor, also demonstrated that the biotinylated casein method can be used to quantitate the amount of trypsin inhibitor in a sample with the slope of the inhibition curve being steep (FIG. 15).

Throughout this application, various publications, including United States patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 2

Spectrum of biotinylated α-casein hydrolysed by different classes proteases

| Proteases[1] | Assay pH[2] | Hydrolysis of biotin-casein by proteases | Sensitivity[3] (ng/100 ul/ sample) |
|---|---|---|---|
| Serine protease | | | |
| trypsin (EC 3.4.21.4) | 7.5 | Yes | 30 |
| elastase (EC 3.4.21.11) | 6.5 | Yes | 4.4 |
| Cysteine protease | | | |
| papain (EC 3.4.22.2) | 6.2 | Yes | 700 |
| Aspartic protease | | | |
| protease XIII (EC 3.4.23.18) | 2.8 | Yes | 222 |
| pepsin (EC 3.4.23.1) | 2.0 | Yes | 641 |
| cathepsin D (EC 3.4.23.5) | 3.0 | Yes | 160 |
| Metaloproteases | | | |
| thermolysin (EC 3.4.24.27) | 7.5 | Yes | 25 |
| collagenase (EC 3.4.24.3) | 7.1 | ?[4] | — |
| Unidentified proteases | | | |
| protease IV | 7.5 | Yes | 200 |
| protease XXXI | 7.5 | Yes | 5500 |

[1]See reference (IUBMB, 1992) for further detail on classes of proteases.
[2]The assay was performed under the optimal pH of each protease (Sigma, 1997).
[3]Sensitivity was defined as the amount of enzyme required to hydrolyse 10% of the biotinylated α-casein.
[4]The biotinylated α-casein were hydrolysed only when the amount of collagenase was more than 50000 ng/100 ul/sample. (The assay media did not contain added zinc, a requirement of the metaloproteinase.)

REFERENCES

Bailey and Nevalainen, 1981. Induction, Isolation and Testing of Stable *Trichoderma reesei* Mutants with Improved

TABLE 1

Relative activity of different enzymes[1]

| Enzyme | Origin | Relative activity compared to lichenase (mean ± SD, n = 12) |
|---|---|---|
| Pure enzymes | | |
| Lichenase (endo 1,3-1,4 glucanase) | Magzyme *Bacillus subtilis* (E.C.3.2.1.73) | 100 ± 4 |
| Endo-β-xylanase | Magzyme *Trichoderma viride* (E.C.3.2.1.32) | 2.1 ± 0.1 |
| Exo-1,3-β-D glucanase | Magzyme Trichoderma sp. (E.C.3.2.1.58) | 6.2 ± 0.3 |
| Partially purified enzymes | | |
| Cellulase (1,4-β-D-glycohydrolase) | (E.C.3.2.1.4) | 101 ± 7 |
| Pullulanase (limit dextranase) | (E.C.3.2.1.41) | 1.8 ± 0.1 |
| α-Amylase | (E.C.3.2.1.1) | 4.3 ± 0.2 |
| Crude enzyme | | |
| RM-1[2] | (Finnfeeds) | 108 ± 4 |

[1]Assay procedures were as described in FIG. 3. All enzyme concentrations were diluted to 5 U of enzyme activity/mL according to the activity values given by the manufacture. The enzymes were then assayed according to procedures in Materials and Methods and FIG. 5. The substrate in all wells was 0.2 biotin-glucan (diluted 1 to 50,000) with hydrolysis time being 15 min and color development time being 30 min at 22° C., assays were carried out with each enzyme. The mean CV was less than 5%.
[2]RM1 contained 900 U/g of β-glucanase (pH 5.0) and a mixture of other enzymes Production of Solubilizing Cellulase. *Enzyme Microbiol. Technol.* 3:153–157.

Bolger and Checovich, 1994. A new protease activity assay using fluorescence polarization. *BioTechniques* 17:585–589.

Bourne and Pierce, 1970. β-Glucan and β-Glucanase in Brewing. *J.Inst.Brew.* 76:328–335.

Bühler, 1991. Double-antibody Sandiwich Enzyme-linked Immunosorbent Assay for Quantisation of Endoglucanase I of *Trichoderma reesei*. *Appl. and Environ. Microbi.* 57:3317–3321.

Cullmann, 1990. Interaction of β-lactamase inhibitors with various β-lactamases. *Chemotherapy* 36:200.

Denalt, et al., 1978. A Simple Reducing Sugar Assay for Measuring β-Glucanase in Malt of Various Microbial Enzyme Preparations. *J. Amer.Soc.Brew.Chem.* 36:18–23.

Edney, 1986. Application of a Simple Radial Gel Diffusion Assay for Endo-β-glucanase Activity in Dietary Enzyme Supplements. *Poultry Sci.* 65:72–77.

Green, 1963. *Biochem. J.* 89:585–591.

Headon, 1993. Activity Analysis of Enzymes Under Field Conditions. In *Enzymes in Animal Nutrition*; Wenk, C., Boessinger, M., Eds., Inst. Nutztierwissenschaften Zürich, Switzerland, 233–240.

Henrissart, et al., 1985. Synergism of Cellulases from *Trichoderma reesei* in the Degradation of Cellulase. *Biotechnol.* 3:722–726.

IUBMB. (1992) Enzyme Nomenclature 1992: *Recommendations of the Nomenclature Committees of IUBMB on the Nomenclature and Classification of Enzymes*. Academic Press, New York.

Kemeny and Challacombe, 1980. ELISA and Other Solid Phase Immunoassays, Theoretical and Practical Aspects. J. Wiley and Sons Ltd. New York, N.Y. 1988

Lorand, 1981. Proteolytic Enzymes Part C. *Method in Enzymology* 80. Academic Press, N.Y.

Martin and Bamforth, 1983. Application of Radial Diffusion Assay for the Measurement of β-Glucanase Activity in Malt. *J.Inst.Brew.* 89:34–37.

McCleary and Shameer, 1987. Assay of Malt β-Glucanase Using Azo-barley Glucan: An Improved Precipitant. *J.Inst.Brew.* 93:87–90.

McClear and Glennie-Holmes, 1985. Enzymatic Quantification of (1–3)(1–4) β-D-Glucan in Barley and Malt. *J.Inst.Brew* 91:285–295.

Miller, et al., 1989. Structure of complex of synthetic HIV-1 protease with a substrate-based inhibitor at 2.3 A resolution. *Science*, 246:1149.

Nieves, et al., 1995. Quantisation of *Acidothermus cellulolyticus* E1 Endoglucanase and *Thermomonospora fusca* E3 Exoglucanase Using Enzyme-linked Immunosorbent Assay (ELISA). *Appl. Biochem. Biotechnol.* 51/52:211–223.

Ondetti and Cushman, 1982. Enzymes of the renin-angiotensin system and their inhibitors. *Ann. Rev. biochem.* 51:283–308.

Pasztai, 1989. Lectins in *Toxicants of Plant Origin, Volume III Protein and Amino Acids*, (Editor) Peter R. Cheeke, CRC Press, Boca Raton Fla., 33431. pgs 29–71)

Rossomando, 1990. Measurement of enzyme activity. *Method in Enzymology* 182:38–50. Academic Press, N.Y.

Sevier, 1976. *Anal. Biochem.* 74:592–596.

Stoll, and Blanchard, 1990. Buffers: principle and practice. *Method in Enzymology* 182:24–38, Academic Press, N.Y.

Twining, 1984. Fluorescein isothiocyanate-labeled casein assay for proteolytic enzymes. *Anal. Biochem.* 143:30–34.

Voss, et al., 1996. Detection of protease activity using a fluorescence-enhancement globular substrate. *BioTechnigues* 20:286–291.

Wirth and Wolf, 1992. Micro-plate Colourimetric Assay for Endo-acting, Cellulase, Xylanase, Chitinase,1,3-β-Glucanase and Amylase Extracted from Forest Soil Horizons. *Soil Biol.Biochem.* 24:511–519.

Wong, 1991. Chemistry of Protein Conjugational and Cross-linking, CRC Press, Inc. Boca-Raton, Fla.

Wood and Bhat, 1988. Methods for Measuring Cellulase Activities. *Methods Enzymol.* 160:87–112.

Yu, 1995. Adsorption and Desorption of Cellulase Components During the Hydrolysis of a Steam-exploded Birch Substrate. *Biotech.Appl.Biochem.* 21:203–216.

Zollner, 1993. *Handbook of Enzyme Inhibitors ($2^{nd}$ edition)* (VCH Publishers, New York).

What is claimed is:

1. A method for determining, via a solid-phase assay, the amount of an inhibitor of hydrolase utilizing the inhibition of biological activity of the hydrolase consisting of the steps of:

a. adding to a vessel having a first specific component conjugated to a first indicator bound to the surface of the vessel a sample containing a known amount of a second specific component having known hydrolase activity and an unknown amount of a third component being an inhibitor of the second component to the first component in a reaction mixture under conditions such that the biological activity between the first and second component will hydrolyze the first component and thereby remove the indicator from the surface of the vessel and the third component will interfere with the reaction between the first and second component;

b. quantitatively reacting the conjugated first component with the second and third components;

c. removing the sample and the indicator removed by the hydrolysis of the first component from the vessel;

d. determining the amount of remaining bound first component conjugated to the indicator wherein there is a direct relationship between the remaining bound conjugated first component and amount of the third component in the sample; and e. quantitating the amount of inhibitor at levels as low as 0.5 to $10^6$ μg enzyme/100 μL/sample in the sample from the amount of the remaining bound first component.

2. The method of claim 1 wherein the hydrolase is a hydrolase capable of degrading a substrate selected from the group consisting of polymeric and non-polymeric substrates.

3. The method of claim 2 wherein the polymeric substrate is selected from the group consisting of protein, polypeptide, carbohydrate, DNA and RNA.

4. The method claim 1 wherein the first indicator is selected from the group consisting of alkaline phosphatase, horseradish peroxidase, colored dye, fluorescent molecule, luminescent molecule, β-galactosidase, urease, tritium, $^{14}C$ and iodination.

5. The method of claim 1, wherein said sample is an extract.

6. The method of claim 1 wherein said determining step includes the step of measuring the amount of remaining first indicator.

* * * * *